_US005652123A_

United States Patent [19]

Caput et al.

[11] Patent Number: 5,652,123
[45] Date of Patent: Jul. 29, 1997

[54] PROTEIN HAVING INTERLEUKIN 13 ACTIVITY, RECOMBINANT DNA CODING FOR THIS PROTEIN, TRANSFORMED CELLS AND MICROORGANISMS

[75] Inventors: Daniel Caput, Toulouse; Pascual Ferrara, Villefranche de Lauragais; Jean-Claude Guillemot, Toulouse; Mourad Kaghad, Ramonville St Agne; Christine Labit-Le Bouteiller, Toulouse; Pascal Leplatois, Cuq Toulza; Marilyn Magazin, Castanet-Tolosan; Adrian Minty, Mervilla, all of France

[73] Assignee: Elf Sanofi, Paris, France

[21] Appl. No.: 371,121

[22] Filed: Jan. 11, 1995

Related U.S. Application Data

[63] Continuation of Ser. No. 938,161, filed as PCT/FR92/00280, Mar. 27, 1992, abandoned.

[30] Foreign Application Priority Data

Mar. 29, 1991 [FR] France ................... 91 03904
Jan. 8, 1992 [FR] France ................... 92 00137

[51] Int. Cl.⁶ .................. C12N 15/24; C07K 14/54
[52] U.S. Cl. ............... 435/69.52; 530/351; 536/23.5; 435/320.1; 435/254.2; 435/252.33; 435/325; 435/365.1; 435/358; 435/360; 424/85.2
[58] Field of Search ................ 536/23.5, 23.51; 435/69.52, 172.1, 240.2, 252.3, 252.33, 320.1, 254.2; 530/351; 424/85.2; 930/141

[56] References Cited

FOREIGN PATENT DOCUMENTS

90/07009  6/1990  WIPO.

OTHER PUBLICATIONS

A.N.J. McKenzie et al. PNAS 90:3735–39, Apr. 1993.
A. Minty et al., Nature 362:248, Mar. 18, 1993.
S.M. Zurawski et al., EMBO J. 12(7):2663–70, 1993.
G. Aversa et al., J. Exp. Med. 178:2213, Dec. 1993.
K.D. Brown, et al., "A Family of Small Inducible Proteins Secreted by Leukocytes are Members of a New Superfamily that Includes Leukocyte and Fibroblast–Derived Inflammatory Agents, Growth Factors, and Indicators of Various Activation Processes", Journal of Immunology, vol. 142, No. 2, Jan. 1989, pp. 679–687.
ATCC Catalogue 17th Ed., 1989, pp. 84–90. R. Gherna et al., eds.

*Primary Examiner*—Stephen Walsh
*Assistant Examiner*—Lorraine Spector
*Attorney, Agent, or Firm*—Foley & Lardner

[57] ABSTRACT

The subject of the present invention is a protein having cytokine type activity, or a precursor of this protein, which comprises the following amino acid sequence (a1):

Gly Pro Val Pro Pro Ser Thr Ala Leu Arg Glu Leu
1           5                   10

Ile Glu Glu Leu Val Asn Ile Thr Gln Asn Gln Lys
          15                  20

Ala Pro Leu Cys Asn Gly Ser Met Val Trp Ser Ile
25              30                  35

Asn Leu Thr Ala Xaa Met Tyr Cys Ala Ala Leu Glu
              40                  45

Ser Leu Ile Asn Val Ser Gly Cys Ser Ala Ile Glu
50              55                  60

Lys Thr Gln Arg Met Leu Ser Gly Phe Cys Pro His
              65                  70

Lys Val Ser Ala Gly Gln Phe Ser Ser Leu His Val
              75                  80

Arg Asp Thr Lys Ile Glu Val Ala Gln Phe Val Lys
85              90                  95

Asp Leu Leu Leu His Leu Lys Lys Leu Phe Arg Glu
              100                 105

Gly Arg Phe Asn
    110 in which Xaa represents Asp or Gly.

27 Claims, 15 Drawing Sheets

Binding site  Hind III

```
    ▼AGCTGGGCTCGCATCTCTCCTTCACGCGCCCGCCGCCCTACCTGAGGCCGCCATCCACGCC
1   ------------------------------------------------------------  60
     CCGAGCCGTAGAGAGGAAGTGCGCGGGCGGCGGGATGGACTCCGGCGGTAGGTGCGG

GGTGAGTCGCGTTCTGCGCCGCCTCCCGCCCTGTGGTGCCTCCTGAACTGCGTCCGCCGTCTA
61  ------------------------------------------------------------ 120
    CCACTCAGCGCAAGACGCGGAGGGCGGACACCACGGAGGACTTGACGCAGGCGGCAGAT

GGTAGGCTCCAAGGGAGCCGGACAAAGGCCCGGTCTCGACCTGAGCTCTAAACTTACCTA
121 ------------------------------------------------------------ 180
    CCATCCGAGGTTCCCTCGGCCTGTTTCCGGGCCAGAGCTGGACTGAGATTTGAATGGAT

GACTCAGCCCGGCTCTCCACGCTTTGCCTGACCCTGCTTGCTCAACTCTACGTCTTTGTTT
181 ------------------------------------------------------------ 240
    CTGAGTCGGGCCGAGAGGTGCGAAACGGACTGGGACGAACGAGTTGAGATGCAGAAACAAA
```

FIG. 1b-1

```
                                                      CGTTTTCTGTTTCTGCGCCGTTACAACTTCAAGGTATGCGCTGGACCTGGCAGGCGGCAT
241   ------------------------------------------------------------  300
                                                      GCAAAAGACAAGACGGGCAATGTTGAAGTTCCATACGGACCCTGGACCGTCCGCCGTA

CTGGGACCCCCTAGGAAGGGCTTGGGGGTCCTCGTGCCCAAGGCAGGGAACATAGTGGTCC
301   ------------------------------------------------------------  360
                                                      GACCCTGGGGATCCTTCCCGAACCCCCAGGAGCACGGGGTTCCGTCCCTTGTATCACCAGG

CAGGAAGGGGAGCAGAGGCATCAGGGTGTCCACTTTGTCTCCGCAGCTCCCTGAGCCTGCA
361   ------------------------------------------------------------  420
                                                      GTCCTTCCCCTCGTCTCCGTAGTCCCACAGGTGAAACAGAGGCGTCGAGGACTCGGACGT

GA
------
CTTCGA▲
    HindIII
```

```
    AAGCCACCCAGCCTATGCATCCGCTCCTCAATCCTCTCCTGTTGGCACTGGGCCTCATG      59
  0                   MetHisProLeuLeuAsnProLeuLeuLeuAlaLeuGlyLeuMet   15
 -4                                                        _____

GCGCTTTGTTGACCAGGTCATTGCTCTCACTTGCCTTGGCGGCTTTGCCTCCCCCAGGC     119
 60 AlaLeuLeuThrValIleAlaLeuThrCysLeuGlyGlyPheAlaSerProGly           35
 16

CCTGTGCCTCCCTCTACAGCCCTCAGGGAGCTCATTGAGGAGCTGGTCAACATCACCCAG    179
120 ProValProProSerThrAlaLeuArgGluLeuIleGluGluLeuValAsnIleThrGln     55
 36                                                   _____

AACCAGAAGGCTCCGCTCTGCAATGGCAGCATGGTATGGAGCATCAACCTGACAGCTGAC    239
180 AsnGlnLysAlaProLeuCysAsnGlySerMetValTrpSerIleAsnLeuThrAlaAsp     75
 56                                  _____

ATGTACTGTGCAGCCCTGATCAACGTGTCAGGCTGCCATGCCATCGAGAAG             299
240 MetTyrCysAlaAlaLeuIleAsnValSerGlyCysSerAlaIleGluLys              95
 76                _____

ACCCAGGAGGATGCTGAGCGGATTCTGCCCGCACAAGGTCTCAGCTGGGCAGTTTTCCAGC   359
300 ThrGlnGluAspAlaGluArgIleLeuProHisLysValSerAlaGlyGlnPheSerSer    115
 96
```

FIG. 2b

```
360  TTGCATGTCCGAGACACCAAAATCGAGGTGGCCCAGTTTGTAAAGGACCTGCTCTTACAT  419
116  LeuHisValArgAspThrLysIleGluValAlaGlnPheValLysAspLeuLeuLeuHis  135

420  TTAAAGAAACTTTTTCGCGAGGACGGTTCAACTGAAACTTCGAAAGCATCATTATTTGC   479
136  LeuLysLysLeuPheArgGluGlyArgPheAsn.                            155

480  AGAGACAGGACCTGACTATTGAAGTTGCAGATTCATTTTTCTTTCTGATGTCAAAAATGT  539

540  CTTGGGTAGGCGGGAAGGAGGGTTAGGGAGGGTAAAATTCCTTAGACCTTAGCCTCAGCC  599

600  TGTGCTGCCCGTCTTCAGCCGACCCTCAGCCCTTCCCCTTGCCCAGGGCTCAGCCTG     659

660  GTGGGCCTCCTCTGTCCAGGCCCTGAGCTCGGTGGACCCAGGATGACATGTCCCTACA    719

720  CCCCTCCCCCTGCCCTAGAGCACACACTGTAGCATTACAGTGGGTGCCCCCCTTGCCAGACAT  779

780  GTGGTGGGACAGGGACCCACTTCACACACAGGCAACTGAGGCAGACAGCAGCTCAGGCAC  839
```

FIG. 2c

```
840   ACTTCTTCTTGGTCTCTTATTTATTATTGTGTTATTAAATGAGTGTGTTGTCACCGTT   899
900   GGGGATTGGGGAAGACTGTGGCTGCTGGCACTTGGGAGCCAAGGGTTCAGAGACTCAGGGC  959
960   CCCAGCACTAAAGCAGTGGACCCCCAGGAGTCCCCTGGTAATAAGTACTGTGTACAGAATTC  1019
1020  TGCTACCTCACTGGGGTCCTGGGGCCTCATCCGAGCCAGGGTCAGGAGAGGG  1079
1080  GCAGAACAGCCGCTCCTGTCTGCCCAGCAGCCTCTCAGCCAACGAGTAATTTAT  1139
1140  TGTTTTCCTCGTATTTAAATATTAAAGAGTTAGCAAAGAGTTAATATATAGAAGGGTA  1199
1200  CCTTGAACACTGGGGGAGGGGACATTGAACAAGTTGTTTCATTGACTATCAAACTGAAGC  1259
1260  CAGAAATAAAGTTGGTGACAGATAAAAAAAAAAAAAAAA....   1300
```

FIG. 3a

```
 1 MetHisProLeuLeuAsnProLeuLeuLeuAlaLeuGlyLeuMetAlaLeuLeuLeuThr  20
 1                              . . . . . . . . MetAlaLeuTrpValThr   6
21 ThrValIleAlaLeuThrCysLeuGlyGlyGlyPheAlaSerProGlyProValProProSer  40
 7 AlaValLeuAlaLeuAlaCysLeuGlyLeuAlaAlaAlaProGlyProValProArgSer  26
41 ThrAla . . . LeuArgGluLeuIleGluGluLeuIleGluLeuValAlaAsnIleThrGlnAsn  56
27 ValSerLeuProLeuThrLeuLysGluLeuIleGluLeuSerAsnIleThrGlnAsp  46
57 GlnLysAlaProLeuCysAsnGlySerMetValTrpSerIleAsnLeuThrAlaAspMet  76
47 Gln . ThrProLeuCysAsnGlySerMetValTrpSerValAspLeuAlaAlaGlyGly  65
```

FIG. 3b

```
 77 TyrCysAlaAlaLeuGluSerLeuIleAsnValSerGlyCysSerAlaIleGluLysThr  96
    | |  |  |     |  |  |   |  |  |  |  |  |  |  |  |  |  |
 66 PheCysValAlaLeuAspSerLeuThrAsnIleSerAsnCysAsnAlaIleTyrArgThr  85

97 GlnArgMetLeuSerGlyPheCysProHisLysValSerAlaGlyGlnPheSerSerLeu 116
    |  |  |  |  |  |  |  |              |  |  |  |  |
 86 GlnArgIleLeuHisGlyLeuCysAsnArgLysAlaAlaProThrThrValSerSer  . 103

117 HisValArgAspThrLysIleGluValAlaAlaGlnPheValLysAspLeuLeuLeuHisLeu 136
    |  |  |  |  |  |  |  |  |  |     |  |  |              |
104 .  LeuProAspThrLysIleGluValAlaAlaHisPheIleThrLysLeuLeuSerTyrThr 122

137 LysLysLeuPheArgGluGlyArgPheAsn 146
    |  |  |  |  |              |
123 LysGlnLeuPheArgHisGlyProPhe . 131
```

FIG. 4a

```
                  ATGCATCCGCTCCCTCAATCC......TCT       23
                      |  ||  |  | ||      |||
            AGCCCACAGTTCTACAGCTCCCTGGTTCT              29

CCTGTTGGCACTGGGCCTCATGGCCCTTTTGTTGACCACGGTCATTGCTC    73
|||  ||||| ||||||||||||||| |||| |||| || ||  ||||||
CTCACTGGCTCTGGGCTTCATGGGCTCTGGGTGACTGCAGTCCTGGCTC    79

TCACTTGCCTTGGCGGGCTTTGCCTCCCCAGGCC......CTGTG       111
|||  ||||||||  |||| ||||  |||||                |||||
TTGCTTGCCTTGGTGTCTCGCCGCCCCAGGCCCGGTGCCAAGATCTGTG    129

CCTCCCCTCTACAGCCCCTCAGGGAGCTCATTGAGGAGCTGGTCAACATCAC  161
|||  | |||| |  ||||||||||||| |||||||||||  ||||||||
TCTCTCCCCTCTGACCCCTTAAGGAGCTTATTGAGGAGCTGAGCAACATCAC  179

CCAGAACCAGAAGGCTCCGCTCTGCAATGGCAGCATGGTATGGGAGCATCA  211
|||   | ||||                  |||||||||||||||||||| —
CCAGAACCAGA...CTCCCCTGTGCAACGGCAGCATGGTATGGGAGTGTGG  226
ACAAGACCAGA
```

```
212 ACCTGACAGCTGACACATGTACTGTGCAGCCCTGGAATCCCTGATCAACGTG 261
    ||||  |  ||| |||   |||  ||||  ||||||| ||||||| |||  |
227 ACCTGGCCGCTGGGCGCGGGTTCTGTGTAGCCCTGGATTCCCTGACCAACATC 276

262 TCAGGCTGCAGTGCCATCGAGAAGACCCAGAGGATGCTGAGCGGATTCTG 311
    |||  |||   ||||||| || ||  ||||| |||    ||||| ||||
277 TCCAATTGCAATGCCATCTACAGGACCCAGAGAGGATATTGCATGGCCTCTG 326

312 CCCGCACAAGGTCTCAGCTGGGCAGTGCTGGGCAGTTTCCAGCTTGCATGTCCGAGACA 361
    |||||  ||| ||  |||   ||   ||     ||   |||  |  ||     ||||
327 TAACCGCAAGGCCCCCAC..........TACGGTCTCCAGCCTCCCCCGATA 367

362 CCAAAATCGAGGTGGCCCAGTTGTAAAGGACCCTGCTCTTACATTTAAAG 411
    ||||||||||||  |||    ||| ||||   |      ||||| ||||
368 CCAAAATCGAAGTAGCCCACTTTATAACAAAACTGCTCAGCTACACAAAG 417

412 AAACTTTTTCGCGAGGGACGGGTTCAACTGA... 441
    ||| ||||||| ||   ||   |||| ||||
418 CAACTGTTTCGCCACGGCCCCCTTCTAATGA... 447
```

FIG. 5a

```
AGCTTGGATAAAAGATCCCCCAGGCCCCTGTGCCCTCTACGGCCCCTCAGGGAGCTCAT
     ----+----+----+----+----+----+----+----+----+----+----+
     ACCTATTTTCTAGGGGTCCGGGACACGGAGGGAGATGCCGGGAGTCCCCTCGAGTA

TGAGGAGCTGGTCAACATCACCCAGAACCAGAAGGCTCCGCTCTGCAATGGCAGCATGGT
     ----+----+----+----+----+----+----+----+----+----+----+
     ACTCCCTCGACCAGTTGTAGTGGGTCTTGGTCTTCCGAGGCGAGACGTTACCGTCGTACCA

ATGGAGCAtCAACCTGACAGCTGACATGTACTGTGCAGCCCTGGAATCCCTGATCAACGT
     ----+----+----+----+----+----+----+----+----+----+----+
     TACCCTCGTaGTTGGACTGTCGACTGTACATGACACGTCGGGACCTTAGGGACTAGTTGCA
```

FIG. 5b

```
GTCAGGCTGCAGTGCCATCGAGAAGACCCAGAGGATGCTGAGCGGATTCTGCCCGCACAA
----+----+----+----+----+----+----+----+----+----+----+----+
CAGTCCGACGTCACGGTAGCTCTTCTGGGTCTCCTACGACTCGCCTAAGACGGGCGTGTT

GGTCTCAGCTGGGCAGTTTTCCAGCTTGCATGTCCGAGACACCAAAATCGAGGTGGCCCA
----+----+----+----+----+----+----+----+----+----+----+----+
CCAGAGTCGACCCGTCAAAAGGTCGAACGTACAGGCTCTGTGGTTTTAGCTCCACCGGGT

GTTTGTAAAGGACCTGCTCTCTTACATTAAAGAAACTTTTTCGCGAGGGACGGTTCAACTG
----+----+----+----+----+----+----+----+----+----+----+----+
CAAACATTTCCTGGACGAGAATGTAAATTTCTTTGAAAAAGCGCTCCCTGCCAAGTTGAC
                                  BamHI

AAACTTCGAAAGCATCATTATTGG
----+----+----+----+----
TTTGAAGCTTTCGTAGTAATAACCCTAG
```

PROTEIN HAVING INTERLEUKIN 13 ACTIVITY, RECOMBINANT DNA CODING FOR THIS PROTEIN, TRANSFORMED CELLS AND MICROORGANISMS

This application is a continuation of parent application Ser. No. 07/938161, filed as PCT/FR92/00280 Mar. 27, 1992, now abandoned.

The present invention relates to a novel protein having cytokine type activity, to the genetic engineering tools for producing it, namely a recombinant DNA and an expression vector carrying this recombinant DNA, to prokaryotic microorganisms and eukaryotic cells containing this recombinant DNA and also to a medicinal product which is useful, in particular, as an immunomodulator, containing this protein as an active principle.

The immune system is well known to comprise cellular elements and soluble substances secreted by the latter, referred to as cytokines. These are proteins which provide for communication between an emitter cell and a target cell belonging either to the immune system or to another biological system of the body. Cytokines have, in general, a so-called pleiotropic biological activity: they can have multiple effects on the target cell: proliferation, differentiation, cytolysis, activation, chemotaxis, and the like. Several of these molecules have already found applications in therapy: for example, interleukin-2 or interferon-α which are used for the treatment of certain tumours by immunotherapy, and myelopoietic factors such as GCSF (granulocyte colony stimulating factor) or GMCSF (granulocyte-monocyte colony stimulating factor) which stimulate blood cell growth and differentiation and thereby enable blood depleted in these cells, for example following chemotherapy, to be enriched therewith.

The following information relating to cytokines is, in particular, available:

1) They correspond to secreted proteins. The secretion of a protein, hence in particular of a cytokine, takes place most often by a mechanism which comprises the cleavage of a hydrophobic amino-terminal region of the translated protein, referred to as a pre peptide sequence or signal peptide, on excretion of the mature protein into the medium (Von Heijne G., 1986, Nucl. Ac. Res., 14, 4683–4690). Most of the peptide sequences of known cytokines actually comprise a signal peptide.

2) Cytokines correspond, in general, to proteins which are inducible, either with other cytokines (K. Matsushima et al, 1988, J. Exp. Med., 167, 1883–1893—Shimizu H. et al, 1990, Mol. Cell. Biol., 10, 561–568), or with chemical agents which activate cell proliferation and differentiation, such as lipopolysaccharides, calcium ionophores, for example calimycin, dibutyryl cyclic AMP, dimethyl sulphoxide, retinoic acid, concanavalin A, phytohaemagglutinin (PHA-P) and phorbol esters, for example phorbol 2-myristate 3-acetate (PMA) (Muegge K. and Durun S. K., 1990, Cytokine 2, 1–8—C. B. Thompson et al, 1989, Proc. Natl. Acad. Sci., 86, 1333–1337), or with antibodies against surface molecules such as the surface antigens CD2, CD3, CD28 and CD40 (Thomson C. B. et al, reference above and Rousset F. et al, 1991, J. Exp. Med., 173, 703–710).

3) Since the induction of cytokines is transient, cytokine messenger RNAs are unstable. For most cytokines, they possess regions rich in A and U, in particular the sequence AUUUA, a consensus instability sequence demonstrated by D. Caput et al, 1986, Proc. Ntl. Acad. Sci. USA, 83, 1670–1674; G. Shaw et al, 1986, Cell, 46, 659–667 and also K. Peppel et al, 1991, J. Exp. Med., 173, 349–355.

4) The large majority of known cytokines are synthesised by cells of the immune system, in particular by monocytes and auxiliary T lymphocytes of the peripheral blood (Ullman K. S. et al., 1989, Ann. Rev. Imm., 8, 421–452 and the work "Macrophage derived cell regulatory factors" by C. Sorg, published in 1989 by Karger-Bâle-Switzerland). Their synthesis is induced with the inducers mentioned in 2).

It is known, moreover, that it is possible, starting from peripheral blood mononuclear cells, consisting mainly of lymphocytes and monocytes, cultured and stimulated using different inducers such as phytohaemagglutinin, phorbol 2-myristate 3-acetate and anti-CD2 monoclonal antibody, to construct a complementary DNA library subtracted from the ubiquitous complementary DNA sequences in animal cells, and hence enriched in complementary DNA coding for cytokines (H. C. Chang et al, Eur. J. Imm., 1989, 19, 1045–1051, P. F. Zipfel et al, 1989, Mol. Cell. Biol, 9, 1041–1048).

It is known, moreover (C. B. Thompson et al, 1989, Proc. Ntl. Acad. Sci., 86, 1333–1337 and Lindsten T. et al, 1989, Science, 244, 339), that the production of cytokines (referred to as lymphokines) by T lymphocytes is greater, and hence corresponds to larger amounts of messenger RNA, with a stimulation using the binary combination phorbol 2-myristate 3-acetate and phytohaemagglutinin or phorbol 2-myristate 3-acetate and anti-CD28 antibody than with phorbol 2-myristate 3-acetate alone, and with the binary combination phorbol 2-myristate 3-acetate and phytohaemagglutinin than with the ternary combination phorbol 2-myristate 3-acetate, phytohaemagglutinin and cyclosporin A, cyclosporin A apparently having an inhibitory effect on the transcription of cytokine messenger RNAs (Thompson et al, reference cited above, and Mattila et al., 1990, EMBO J., 9, 4425–4433).

This differential expression of cytokine messenger RNAs under different conditions of stimulation may be used for a screening, referred to as differential screening, of a complementary DNA library containing sequences coding for cytokines with the object of selecting the latter sequences (see, in particular, Dworkin et al, 1980, Dev. Biol., 76, 449–464, Cochran B. M. et al, 1983, Cell, 33, 939–947 and Zipfel P. F. et al, 1989, Mol. Cell. Biol., 9, 1041–1048). It is, in effect, possible, starting from two messenger RNAs corresponding to two cell stimulation states referred to here as stimulation state 1 and stimulation state 2, stimulation state 2 being assumed to be richer in messenger RNAs coding for a cytokine than state 1, to construct two radioactive probes referred to as probe 1 and probe 2, respectively, which are transcripts obtained using the reverse transcriptase of these two messenger RNAs. These two probes are hybridised with bacterial colonies containing complementary DNA sequences of the library. Bacterial colonies containing a complementary DNA whose messenger RNA changes in abundance between the two activation states will give differential signals with the two probes, the hybridation being greater in the case of the clones selected (which correspond to inducible proteins) for probe 2 than for probe 1.

It is known, moreover, that COS cells, monkey kidney cells expressing the T antigen of the SV40 virus (Gluzman, Y., Cell, 23, 1981, 175–182), which permit the replication of vectors containing the origin of replication of SV40 virus DNA, constitute hosts of choice for studying the expression of genes in animal cells and the secretion of the proteins expressed. The secretion of a protein in these cells indicates that it is secreted by the cell which produces it naturally (H. C. Chang et al., Eur. J. Imm., 1989, 19, 1045–1051 and W. Y. Weiser et al., 1989, Proc. Ntl. Acad. Sci. USA, 86, 7522–7526).

The subject of the present invention is a protein having cytokine type activity, or a precursor of this protein, which comprises the following amino acid sequence (a1)(SEQ ID NO:1):

Gly Pro Val Pro Pro Ser Thr Ala Leu Arg Glu Leu
1               5                   10

Ile Glu Glu Leu Val Asn Ile Thr Gln Asn Gln Lys
          15                  20

Ala Pro Leu Cys Asn Gly Ser Met Val Trp Ser Ile
25              30                  35

Asn Leu Thr Ala Xaa Met Tyr Cys Ala Ala Leu Glu
              40                  45

Ser Leu Ile Asn Val Ser Gly Cys Ser Ala Ile Glu
50              55                  60

Lys Thr Gln Arg Met Leu Ser Gly Phe Cys Pro His
              65                  70

Lys Val Ser Ala Gly Gln Phe Ser Ser Leu His Val
75              80

Arg Asp Thr Lys Ile Glu Val Ala Gln Phe Val Lys
85              90                  95

Asp Leu Leu Leu His Leu Lys Lys Leu Phe Arg Glu
              100                 105

Gly Arg Phe Asn
110 in which Xaa represents Asp or Gly, or a sequence possessing a high degree of homology with the sequence (a1).

A high degree of homology means here a homology of identity (ratio of identical amino acids to the total number of amino acids) of at least 80%, and preferably at least 90%, of the amino acid sequences when they are aligned on the basis of maximal homology according to the optimal sequence alignment method of Needleman and Wunsch, 1970, J. Mol. Biol., 48, 443–453. This algorithmic method, which considers all possible alignments and creates an alignment in which the largest possible number of identical amino acids are paired and the number of holes in the aligned sequences is minimal, is used, in particular, in the University of Wisconsin's UWGCG software: Devereux et al, 1984, Nucl. Ac. Res., 12, 8711–8722—GAP option.

The already known peptide sequence most closely related to that of the sequence (a1) of 112 amino acids is that of 132 amino acids deduced from the complementary DNA of the mouse protein P600 described by K. D. Brown et al., 1989, J. Imm., 142, 679–687 (protein expressed by mouse TH2 lymphocytes, the function of which has not been elucidated). A comparison of these peptide sequences using the method of Needleman and Wunsch, 1970, J. Mol. Biol., 48, 443–453, shows that 63 amino acids out of 112 are identical, equivalent to an approximately 56% homology of identity.

The protein of the present invention is a protein secreted, in particular, by T lymphocytes and inducible in the latter with phorbol 2-myristate 3-acetate, this induction being—as expected for a cytokine (see text above)—amplified by phytohaemagglutinin or anti-CD28 monoclonal antibody, with an inhibitory effect on this increase in the case of stimulation with phytohaemagglutinin in the additional presence of cyclosporin A. The protein according to the invention, referred to as protein NC30, is hence a novel human lymphokine possessing cytokine type immunomodulatory activities (cell proliferation, cell activation, chemotaxis and regulation of the synthesis of other cytokines). It acts on at least two key cells of the immune system: monocytes and B lymphocytes. It is hence a novel interleukin. Some of its properties are held in common with interleukin-4: inhibition of the synthesis of interleukin-1β and interleukin-6 by LPS-activated peripheral blood monocytes, and modulation of the expression of the CD23 antigen on tonsil B lymphocytes. These two properties are also those of interleukin-4 (W. Paul, 1991, Blood, 77, 1959 and Waal Malefyt et al., 1991, J. Exp. Med., 174, 1199–1220).

The protein of the invention is a novel interleukin, of the lymphokine type. It is of interest as a principle of a medicinal product which is useful for the treatment of tumours and some infectious or inflammatory states by immunomodulation.

The protein of the invention can comprise, immediately upstream of the sequence (a1), one or more amino acids, especially the sequence: Ser-Pro.

This protein is preferably in a form which has an apparent molecular mass, determined by polyacrylamide gel electrophoresis in the presence of SDS, of 9.0±2 or 16.0±2 kDa. It is advantageously N-glycosylated, especially when it has an apparent molecular mass of 16.0±2 kDa.

It is advantageous that this protein should possess a degree of purity, determined by polyacrylamide gel electrophoresis in the presence of SDS and visualisation with silver, of greater than 70%, and preferably greater than 90%.

The subject of the invention is also a recombinant DNA, characterised in that it codes for the above protein, which can then be obtained from the cell lysate, or advantageously for a precursor of the above protein. This precursor preferably comprises a signal sequence.

This signal sequence, chosen in accordance with the host cell, has the function of enabling the recombinant protein to be exported from the cytoplasm, thereby enabling the recombinant protein to assume a conformation close to that of the natural protein and considerably facilitating its purification. This signal sequence may be cleaved, either in several steps by a signal peptidase liberated by the mature protein, or in several steps when this signal sequence comprises, in addition to the sequence removed by the signal peptidase, referred to as a signal peptide or presequence, a sequence removed later during one or more proteolytic events, referred to as a prosequence.

The sequence coding for the mature protein is, for example, one of the following sequences, (Na1) or (Na1'):

(Na1) (SEQ ID NO: 2):

| | | | |
|---|---|---|---|
| GGCCCTGTGC | CTCCCTCTAC | AGCCCTCAGG | GAGCTCATTG |
| AGGAGCTGGT | CAACATCACC | CAGAACCAGA | AGGCTCCGCT |
| CTGCAATGGC | AGCATGGTAT | GGAGCATCAA | CCTGACAGCT |
| GACATGTACT | GTGCAGCCCT | GGAATCCCTG | ATCAACGTGT |
| CAGGCTGCAG | TGCCATCGAG | AAGACCCAGA | GGATGCTGAG |
| CGGATTCTGC | CCGCACAAGG | TCTCAGCTGG | GCAGTTTTCC |
| AGCTTGCATG | TCCGAGACAC | CAAAATCGAG | GTGGCCCAGT |
| TTGTAAAGGA | CCTGCTCTTA | CATTTAAAGA | AACTTTTTCG |
| CGAGGGACGG | TTCAAC | | |

(Na1') (SEQ ID NO: 24):

```
GGCCCTGTGC CTCCCTCTAC AGCCCTCAGG GAGCTCATTG
AGGAGCTGGT CAACATCACC CAGAACCAGA AGGCTCCGCT
CTGCAATGGC AGCATGGTAT GGAGCATCAA CCTGACAGCT
GGCATGTACT GTGCAGCCCT GGAATCCCTG ATCAACGTGT
CAGGCTGCAG TGCCATCGAG AAGACCCAGA GGATGCTGAG
CGGATTCTGC CCGCACAAGG TCTCAGCTGG GCAGTTTTCC
AGCTTGCATG TCCGAGACAC CAAAATCGAG GTGGCCCAGT
TTGTAAAGGA CCTGCTCTTA CATTTAAAGA AACTTTTTCG
CGAGGGACGG TTCAAC
```

For an expression in prokaryotic microorganisms such as, for example, *Escherichia coli*, this signal sequence can be either a sequence derived from the sequence coding for a natural precursor of a protein exported by a prokaryotic microorganism (for example the OmPA signal peptide [Ghrayeb et al., 1984, EMBO Journal, 3, 2437–2442] or the alkaline phosphatase signal peptide [Michaelis et al., J. Bact., 1983, 154, 366–374]), or a non-endogenous sequence originating from a sequence coding for a eukaryotic precursor (for example the signal peptide of one of the natural precursors of human growth hormone), or a sequence coding for a synthetic signal peptide (for example that described in French Patent Application No. 2,636,643, of sequence (SEQ ID NO:3):

Met Ala Pro Ser Gly Lys Ser Thr Leu Leu Leu Leu
1              5                   10
Phe Leu Leu Leu Cys Leu Pro Ser Trp Asn Ala Gly
         15                  20
Ala)
25

For an expression in eukaryotic cells such as ascomycetes, for example *Saccharomyces cerevisiae* yeast or the filamentous fungus *Cryphonectria parasitica*, this signal sequence is preferably a sequence derived from a sequence coding for a natural precursor of a protein secreted by these cells, for example, for yeast, the invertase precursor (Patent Application EP 0,123,289) or the precursor of the prepro sequence of the alpha pheromone (Patent Application DK 2484/84), or for *Cryphonectria parasitica*, the precursor of the prepro sequence of endothiapepsin, of sequence:

Met Ser Ser Pro Leu Lys Asn Ala Leu Val Thr Ala
1              5                   10
Met Leu Ala Gly Gly Ala Leu Ser Ser Pro Thr Lys
         15                  20
Gln His Val Gly Ile Pro Val Asn Ala Ser Pro Glu
    25                  30                  35
Val Gly Pro Gly Lys Tyr Ser Phe Lys Gln Val Arg
              40                  45
Asn Pro Asn Tyr Lys Phe Asn Gly Pro Leu Ser Val
         50                  55                  60
Lys Lys Thr Tyr Leu Lys Tyr Gly Val Pro Ile Pro
                    65                  70
Ala Trp Leu Glu Asp Ala Val Gln Asn Ser Thr Ser
              75                  80
Gly Leu Ala Glu Arg
85

For an expression in animal cells, either a signal sequence of an animal cell protein known to be exported—for example a sequence coding for the signal peptide of one of the natural precursors of human growth hormone which is already known to permit the secretion of interleukin-2 (see French Patent Application 2,619,711)—or one of the following four signal sequences (b1), (b2), (b3) and (b4):

(b1) (SEQ ID NO: 5)
Met His Pro Leu Leu Asn Pro Leu Leu Leu Ala Leu
1              5                   10
Gly Leu Met Ala Leu Leu Leu Thr Thr Val Ile Ala
         15                  20
Leu Thr Cys Leu Gly Gly Phe Ala
    25                  30

(b2) (SEQ ID NO: 6)
Met His Pro Leu Leu Asn Pro Leu Leu Leu Ala Leu
1              5                   10
Gly Leu Met Ala Leu Leu Leu Thr Thr Val Ile Ala
         15                  20
Leu Thr Cys Leu Gly Gly Phe Ala Ser Pro
    25                  30

(b3) (SEQ ID NO: 7)
Met Ala Leu Leu Leu Thr Thr Val Ile Ala Leu Thr
1              5                   10
Cys Leu Gly Phe Ala
         15

(b4) (SEQ ID NO: 8)
Met Ala Leu Leu Leu Thr Thr Val Ile Ala Leu Thr
1              5                   10
Cys Leu Gly Gly Phe Ala Ser Pro
         15                  20 advantageously encoded by the following sequences (Nb1), (Nb2), (Nb3) and (Nb4), respectively:

(Nb1) (SEQ ID NO: 9)
```
ATGCATCCGC TCCTCAATCC TCTCCTGTTG GCACTGGGCC
TCATGGCGCT TTTGTTGACC ACGGTCATTG CTCTCACTTG
CCTTGGCGGC TTTGCC
```

(Nb2) (SEQ ID NO: 10)
```
ATGCATCCGC TCCTCAATCC TCTCCTGTTG GCACTGGGCC
TCATGGCGCT TTTGTTGACC ACGGTCATTG CTCTCACTTG
CCTTGGCGGC TTTGCCTCCC CA
```

```
(Nb3) (SEQ ID NO: 11)
            ATGGCGCTTT    TGTTGACCAC   GGTCATTGCT   CTCACTTGCC
            TTGGCGGCTT    TGCC (Nb4) (SEQ ID NO: 12)
            ATGGCGCTTT    TGTTGACCAC   GGTCATTGCT   CTCACTTGCC
            TTGGCGGCTT    TGCCTCCCCA
``` is used as a signal sequence.

The invention also relates to an expression vector which carries the recombinant DNA defined above with the means needed for its expression.

For an expression in prokaryotic microorganisms, especially in *Escherichia coli*, the recombinant DNA must be inserted in an expression vector containing, in particular, an effective promoter, followed by a ribosome binding site upstream of the gene to be expressed, as well as an effective transcription stop sequence downstream of the gene to be expressed. This plasmid must also contain an origin of replication and a selection marker. All these sequences must be chosen in accordance with the host cell.

For an expression in eukaryotic cells, the expression vector according to the invention carries the recombinant DNA defined above with the means needed for its expression, for its replication in eukaryotic cells and for the selection of the transformed cells. Preferably, this vector carries a selection marker, chosen, for example, so as to complement a mutation of the recipient eukaryotic cells, which enables the cells which have integrated the recombinant DNA in a high copy number, either in their genome or in a multicopy vector, to be selected.

For an expression in eukaryotic cells such as yeast, for example *Saccharomyces cerevisiae*, it is appropriate to insert the recombinant DNA between, on the one hand sequences recognised as an effective promoter, and on the other hand a transcription terminator. The promoter-coding sequence-terminator assembly, referred to as an expression cassette, is either cloned into a single-copy or multicopy plasmid vector for yeast, or integrated in multicopy form in the yeast genome.

For an expression in eukaryotic cells such as those of filamentous fungi of the ascomycete group, for example those of the genera Aspergillus, Neurospora, Podospora, Trichoderma or Cryphonectria, the expression vector according to the invention carries the recombinant DNA defined above with the means needed for its expression, and optionally a selection marker and/or telomeric sequences. It is, in effect, possible to select transformants which have integrated a DNA of interest using a selection marker located either on the same vector as the DNA of interest or on another vector, these two vectors then being introduced by cotransformation. The recombinant DNA of the invention may be either integrated in the genome of the filamentous fungi, or preserved in extrachromosomal form by means of sequences enabling this DNA to be replicated and split off.

For an expression in animal cells, in particular in Chinese hamster ovary CHO cells, the recombinant DNA is preferably inserted into a plasmid (for example derived from pBR322) containing either a single expression unit, into which there is inserted the recombinant DNA of the invention and optionally a selection marker, in front of an effective promoter, or two expression units. The first expression unit contains the above recombinant DNA, preceded by an effective promoter (for example the SV40 early promoter). The sequence around the initiation ATG is preferably chosen in accordance with the consensus sequence described by Kozak (M. Kozak (1978) Cell., 15, 1109–1123). An intron sequence, for example the mouse α-globin intron, may be inserted upstream of the recombinant DNA, as well as a sequence containing a polyadenylation site, for example a SV40 polyadenylation sequence, downstream of the recombinant gene. The second expression unit contains a selection marker, for example a DNA sequence coding for dihydrofolate reductase (enzyme hereinafter abbreviated to DHFR). The plasmid is transfected into animal cells for example CHO dhfr⁻ cells (incapable of expressing DHFR). A line is selected for its resistance to methotrexate: it has integrated in its genome a high number of copies of the recombinant DNA and expresses the latter at a sufficient level.

The invention also relates to prokaryotic microorganisms transformed by the expression vector defined above, especially those of the species *Escherichia coli*, as well as to eukaryotic cells which contain the recombinant DNA defined above with the means needed for its expression. This DNA can have been introduced by transformation with the above expression vector or with the recombinant DNA of the invention itself, which can sometimes be integrated directly in the genome at a locus which permits its expression.

Advantageous eukaryotic cells are animal cells.

The recombinant DNA can, for example, have been introduced into these cells by transfection with the above expression vector, by infection by means of a virus or retrovirus carrying it or by microinjection. Preferred animal cells are CHO cells, especially CHO dhfr⁻ cells, from which it is possible to obtain lines which are highly productive of the protein of the invention. COS cells also constitute an advantageous host for obtaining this protein.

Other advantageous eukaryotic cells are yeast cells, especially of *Saccharomyces cerevisiae*.

The invention also relates to a method for preparing the protein defined above, which comprises a step of culturing the above animal cells, or cells of this yeast, followed by isolation and purification of the recombinant protein.

The invention also relates to the recombinant protein capable of being obtained by a method which comprises a step of culturing these animal cells, or cells of this yeast, followed by isolation and purification of the recombinant protein.

The subject of the invention is hence also the medicinal product, which is useful, in particular, in oncology and in the treatment of some infectious states and some inflammatory states by immunomodulation, which contains as active principle the protein defined above, in a pharmaceutically acceptable excipient. Such medicinal products may be used alone or in combination with other active agents: for example one or more other cytokines.

A better understanding of the invention will be gained from the description below, divided into sections, which comprises experimental results and a discussion of the latter. Some of these sections relate to experiments performed with the object of carrying out the invention, and others to examples of embodiment of the invention which are naturally given purely by way of illustration.

A large part of the collective techniques described in these sections, which are well known to a person skilled in the art, is described in detail in the work by Sambrook, Fritsch and Maniatis: "Molecular cloning: a Laboratory manual" published in 1989 by Cold Spring Harbor Press editions, New York (2nd edition).

BRIEF DESCRIPTION OF THE DRAWINGS

A better understanding of the description below will be gained from FIGS. 1a, 1b, 1c, 2, 3, 4, 5, 6 and 7.

FIG. 1b (SEQ ID NO:13) shows the sequence of the "HindIII binding site"—HindIII synthetic fragment used for assembling plasmid pSE1.

FIG. 2 (SEQ ID NO:15) shows the nucleotide sequence of NC30 cDNA and, next to it, the deduced amino acid sequence, the two Met residues capable of initiating translation being underlined, the probable cleavage sites of the signal peptide being indicated by vertical arrows and the four possible N-glycosylation sites having broken underlining.

FIG. 3 and FIG. 4 show, respectively, the alignment, on the basis of maximal homology according to the method of Needleman and Wunsch, 1970, J. Mol. Biol., 48, 443–453, of the amino acid sequence deduced from NC30 cDNA (upper line) (SEQ ID NO: 16) and the sequence deduced from the cDNA of the mouse protein P600 (lower line) (SEQ ID NO:25), and the alignment according to this method of the coding portion of NC30 cDNA (upper line) (nucleotides 15–445 of SEQ ID NO:15) and the coding portion of the cDNA of the P600 protein (lower line) (SEQ ID NO:26).

FIG. 5 (SEQ ID NO:17) shows the sequence of the fragment B, the silent mutation site relative to NC30 cDNA being indicated by an asterisk.

SECTION 1

Figure 1A:
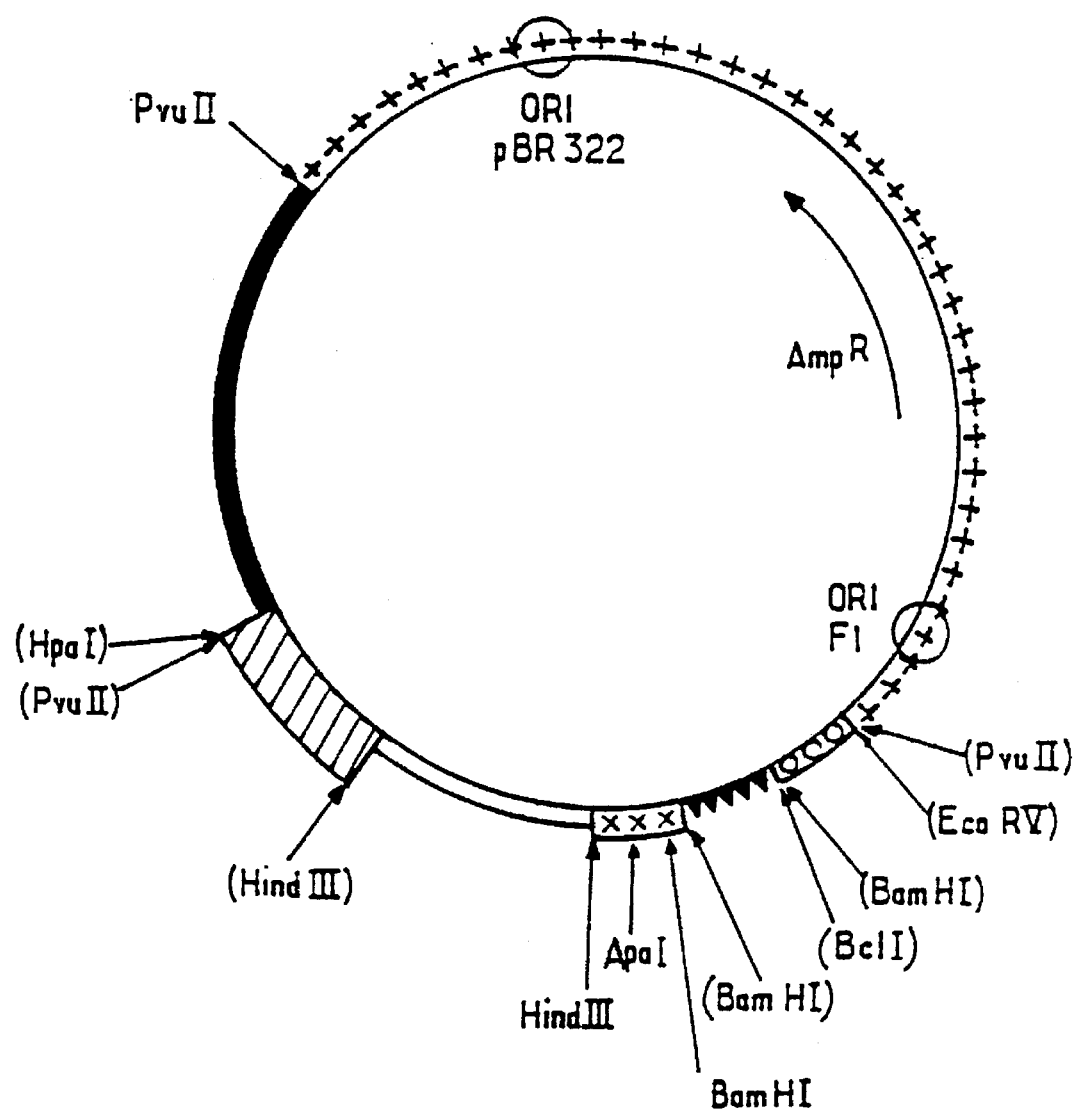
FIG. 1a shows an assembly map of plasmid pSE1, a plasmid for cloning in E. coli and expression in animal cells, the sites which have disappeared by ligation being noted in brackets. The symbols used in this figure will be defined in the description of this plasmid (section 2).

Culture and stimulation of peripheral blood mononuclear cells using PMA and PHA-P. Preparation of the messenger RNA used to make the complementary DNA library 1) Culture and stimulation of peripheral blood mono-nuclear cells:

From bags of peripheral blood (drawn from three healthy volunteers in a blood transfusion centre) which has been subjected beforehand to cytapheresis and a Ficoll gradient (Pharmacia Boyum A., 1968, Scand. J. Clin. Lab. Invest., 21, p. 77–89), a cell fraction enriched with peripheral blood mononuclear cells (PBMNC) of the following approximate composition: 70% lymphocytes, 25% monocytes and 5% granulocytes (cell counting using a Coulter—Model S-Plus IV cell counter), is withdrawn.

The cells are collected in a 250-ml flask and then centrifuged at 300 g for 10 min at 37° C. The supernatant is removed and the cell pellet is rinsed with 50 ml of medium based on glucose, inorganic salts, amino acids and vitamins, referred to as RPMI medium (Gibco BRL RPMI 1640 medium) and then centrifuged again under the same conditions.

The cell pellet is then taken up with 500 ml of RPMI medium supplemented with 10% of fetal calf serum (Gibco BRL—ref. 013-06290H) and with the addition of 10 units of penicillin and 10 µg of streptomycin (Gibco ref. 043-05140D penicillin/streptomycin solution) per ml of medium, as well as L-glutamine (Gibco BRL—ref. 043-05030D) to 2 mM final.

A portion of the cell suspension is distributed, for the purpose of separation of adherent cells and non-adherent cells, on the basis of approximately 100 ml per dish, in four large square culture dishes (245×245×20 mm-Nunc—ref. 166508) and incubated for 1 h at 37° C. It is known, in effect, that most of the monocytic cells adhere to the culture dish while most of the lymphocytic cells remain in suspension.

The non-adherent cells are aspirated using a pipette and cultured in Falcon type culture flasks of surface area 175 $cm^2$ in the presence of RPMI medium supplemented as described above and with the addition of 10 ng/ml of phorbol 2-myristate 3-acetate (PMA) (Sigma-ref. P8139) and 5 µg/ml of phytohaemagglutinin (PHA-P) (Sigma-ref. L8754), at 37° C. in the presence of 5% $CO_2$ for 24 h.

To the adherent cells, 100 ml of RPMI medium supplemented as described above and with the addition of 10 ng/ml of PMA and 5 µg/ml of PHA-P are added. The cells are incubated at 37° C. in the presence of 5% (v/v) $CO_2$ for 5 h.

The remainder of the cell suspension, hereinafter referred to as the total cells, is distributed in 4 large square culture dishes and incubated in the presence of RPMI medium supplemented as described above and with the addition of 10 ng/ml of PMA and 5 µg/ml of PHA-P, at 37° C. in the presence of 5% (v/v) $CO_2$ for 5 h for the first two dishes and 24 h for the other two.

Approximately 2 h before the end of the incubation, 10 µg/ml of cycloheximide (Sigma ref. C6255) (translation inhibitor which increases the stability of cytokine RNAs: see Lindsten et al, 1989, Science, 244, 339–344) is added to the culture medium of these different cells, and incubation is continued for 2 h at 37° C.

2) Preparation of the messenger RNA:

a) Extraction of the messenger RNA

The cells are recovered in the following manner:

- the adherent cells are washed twice with PBS buffer (phosphate-buffered saline ref. 04104040-Gibco BRL), then scraped off with a rubber scraper and centrifuged. A cell pellet is thereby obtained, referred to as pellet A.
- for the non-adherent cells, after agitation of the flask containing the cell suspension, the cell suspension is withdrawn and centrifuged. The cell pellet is thereby obtained, referred to as cell pellet NA.
- for the total cells, the adherent fraction is washed twice with PBS buffer, scraped off as above and then centrifuged. The non-adherent fraction is centrifuged. The two cell pellets obtained will subsequently be combined. The combination thereof is referred to as cell pellet T(5 h) for the total cells incubated for 5 h, and T(24 h) for the total cells incubated for 24 h.

Cell pellets A, NA, T(5 h) and T(24 h) are frozen and stored at −80° C.

Each frozen cell pellet is suspended in the lysis buffer of the following composition: 5M guanidine thiocyanate, 50 mM Tris(hydroxymethyl)aminomethane, pH 7.5, 10 mM EDTA. The suspension is sonicated using an Ultra-Turax No. 231,256 sonicator (Janke and Kunkel) at maximum power for 4 cycles of 20 s. β-Mercaptoethanol is added to 0.2M and a further sonication cycle of 30 s is applied. Lithium chloride is added to 3M. The suspension is cooled to 4° C. and left standing at this temperature for 48 h. The RNA is then isolated by centrifugation for 60 min. The RNA pellet is washed once with 3M lithium chloride solution, centrifuged again and then taken up in a buffer of the following composition: 1% SDS, 5 mM EDTA and 10 mM Tris-HCl, pH 7.5, with the addition of 1 mg/ml of proteinase K (Boehringer Mannheim, GmbH). After incubation at 40° C. for 1 h, the RNA solution is extracted with a phenol/ chloroform mixture. The RNA contained in the aqueous phase is precipitated at −20° C. using ammonium acetate solution of final concentration 0.3M and 2.5 volumes of ethanol. The suspension is centrifuged at 15,000 g for 30 min and the pellet is kept.

b) Purification of the poly(A)⁺ fraction of the RNA

The pellet is taken up in 1 ml of buffer of composition 10 mM Tris-HCl, pH 7.5, 1 mM EDTA, referred to as TE buffer, and suspended by vortexing. Type 3 oligo(dT)-cellulose (marketed by Collaborative Research Inc, Biomedicals Product Division) is prepared according to the manufacturer's recommendations. The RNA is applied to the oligo(dT)-cellulose, agitated gently to suspend the beads and then heated for 1 min to 65° C.

The suspension is adjusted to 0.5M NaCl and then agitated gently for 10 min. The suspension is then centrifuged for 1 min at 1000 g, the supernatant is removed and the pellet is washed twice with 1 ml of TE buffer containing 0.5M NaCl. The supernatants are removed. Elution of the polyadenylated fraction of the RNA (consisting of messenger RNAs) is obtained by suspending the beads in 1 ml of TE buffer and then heating this suspension to 60° C. for 1 min, followed by agitation for 10 min on a tilting-plate shaker. The suspension is then centrifuged for 1 min at 1000 g, enabling the supernatant containing free messenger RNAs in solution to be recovered. The above set of operations (starting from the elution) is repeated twice. The supernatants thereby obtained are combined, the residual beads are removed by centrifugation and the supernatant is precipitated with three volumes of ethanol and an NaCl solution of final concentration 0.3M.

From the cell pellets A, NA, T(5 h) and T(24 h), four RNA-poly(A)⁺ samples are thereby obtained, hereinafter designated RNA-poly(A)⁺-A, RNA-poly(A)⁺-NA, RNA-poly(A)⁺-T(5 h) and RNA-poly(A)⁺-T(24 h).

SECTION 2

Preparation of a complementary DNA library enriched in sequences specific to peripheral blood mononuclear cells 1) Construction of the cloning vector pSE1:

The strategy employed makes use of fragments obtained from pre-existing plasmids available to the public, and of fragments prepared synthetically according to techniques which are now in common use. The cloning techniques employed are those described by Sambrook et al, in "Molecular Cloning, a Laboratory manual" (Cold Spring Harbor Laboratory, 1989). Oligonucleotide synthesis is carried out using a Biosearch 8700 DNA synthesiser.

A better understanding of the description below will be gained by reference to FIG. 1a.

This plasmid was constructed by successive ligations of the following elements:

a) a 2525-bp PvuII-PvuII fragment—symbolised by +++++++ in FIG. 1a—obtained by complete digestion of plasmid pTZ18R (Pharmacia) using the restriction enzyme PvuII. This fragment contains the origin of replication of the phage f1 (designated ORI F1 in FIG. 1a), a gene (designated Amp^R in FIG. 1a) carrying resistance to ampicillin and the origin of replication (designated ORI pBR322 in FIG. 1a) permitting replication of this plasmid in E. coli. The first blunt PvuII site disappears on ligation with the blunt EcoRV site (which also disappears) of the fragment described in g).

b) a 1060-bp PvuII-HpaI fragment—symbolised by ▬ in FIG. 1a—of type 5 adenovirus DNA between positions 11299 (PvuII restriction site) and 10239 (HpaI restriction site) (Dekker and Van Ormondt, Gene, 27, 1984, 115–120) containing the information for the VA-I and VA-II RNAs. The blunt HpaI site disappears on ligation with the blunt PvuII site (which also disappears) of the fragment described in c). The ApaI site at position 11 218 has been removed by cleavage using the enzyme ApaI, treatment using the exonuclease phage T4 DNA polymerase and religation.

c) a 344-bp PvuII-HindIII fragment—symbolised by /////// in FIG. 1a—derived from SV40 virus DNA, obtained by complete digestion using the restriction enzymes PvuII and HindIII. This fragment contains the origin of replication and the early promoter of SV40 virus DNA (ref. B. J. Byrne et al., Proc. Ntl. Acad. Sci. USA (1983), 80, 721–725).

Figure 1C:
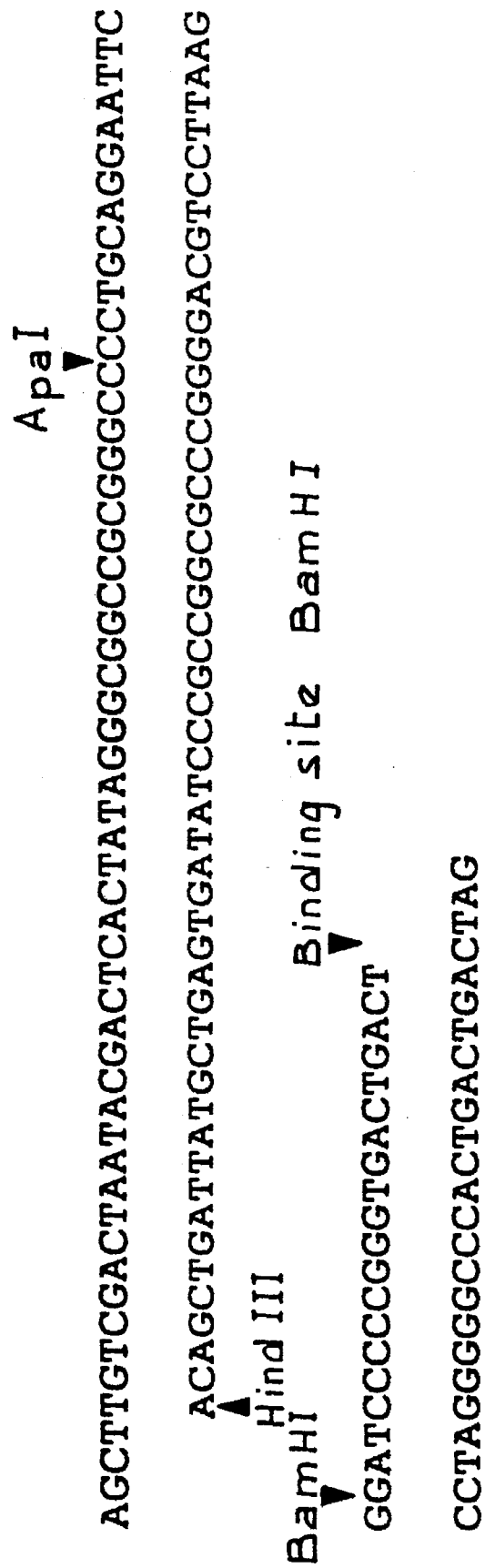
FIG. 1c (SEQ ID NO:14) shows the sequence of the HindIII—"BamHI binding site" synthetic fragment.

The HindIII site disappears on ligation with the HindIII binding site of the fragment described in d).

d) a 419-bp "HindIII binding site"—HindIII synthetic fragment—symbolised by = in FIG. 1a—whose sequence, given in FIG. 1b, contains a sequence closely related to the untranslated 5' sequence of the HTLV-1 virus (R. Weiss et al, "Molecular Biology of Tumor Viruses—part 2-2nd ed—1985—Cold Spring Harbor Laboratory—p. 1057) and the distal intron of the mouse α-globin gene (Y. Nishioka et al, 1979, Cell, 18, 875–882).

e) a HindIII—"BamHI binding site" synthetic fragment—symbolised by XXXXXXX in FIG. 1a—containing the phage T7 RNA polymerase promoter, as well as a polylinker containing, in particular, the ApaI and BamHI cloning sites, whose sequence is shown in FIG. 1c.

f) a 240-bp BamHI-BclI fragment—represented by ▲▲▲ in FIG. 1a—a small fragment obtained by complete digestion of the SV40 virus using the enzymes BclI and BamHI, which contains the SV40 late polyadenylation site (M. Fitzgerald et al.; Cell, 24, 1981, 251–260). The BamHI and BclI sites disappear on ligation with the "BamHI binding site" of the fragment described in e) and the BamHI site (which also disappears) of the fragment described in g), respectively.

g) a 190-bp BamHI-EcoRV fragment—symbolised by OOOOOOO in FIG. 1a—a small fragment derived from plasmid pBR322 after complete digestion using the enzymes EcoRV and BamHI.

Plasmid pSE1 hence contains the elements needed for its use as a cloning vector in E. coli (origin of replication in E. coli and gene for resistance to ampicillin, originating from plasmid pTZ18R) and also as a vector for expression in animal cells (promoter, intron, polyadenylation site, origin of replication of the SV40 virus), and for copying it in single-stranded form for the purpose of sequencing (origin of replication of the phage f1).

2) Formation of a complementary DNA library enriched in sequences specific to peripheral blood mononuclear cells:

The cloning technique used is that described by Caput et al, (primer-adapter technique: Caput et al, Proc. Natl. Acad. Sci. U.S.A., 1986, 83, 1670–1674).

It consists, on the one hand in digesting the vector pSE1 with ApaI and adding a poly(dC) tail to the protruding 3' end, and then in digesting the plasmids thereby obtained with the endonuclease BamHI. The fragment corresponding to the vector is purified on a Sepharose CL-4B (Pharmacia)

column. It hence comprises a poly(dC) tail at one end, the other end being cohesive, of the BamHI type.

On the other hand, the poly(A)$^+$ RNAs obtained at the end of section 1 are subjected to reverse transcription using a primer whose sequence is as follows (SEQ ID NO:18)

5'<GATCCGGGCC CTTTTTTTTT TTT<3'

Thus, the cDNAs possess at their 5' end the sequence GATCC complementary to the BamHI cohesive end.

The RNA-DNA hybrids obtained by the action of reverse transcriptase are subjected to an alkaline hydrolysis which enables the RNA to be removed. The single-stranded cDNAs are then subjected to a treatment with terminal transferase so as to add poly(dG) units at the 3' end, and purified by 2 cycles on a Sepharose CL-4B column.

These cDNAs are hybridised with RNA-poly(A)$^+$ originating from COS3 line cells (monkey kidney cell line expressing the SV40 virus T antigen: see Y. Gluzman, 1981, Cell, 23, 175–182) prepared as described in section 1 subsection 2).

The unhybridised cDNAs are isolated (fraction enriched in DNA complementary to the messenger RNAs specific to peripheral blood mononuclear cells).

These cDNAs are inserted in single-stranded form into the vector pSE1. A second oligonucleotide (the adapter) complementary to the primer is necessary to generate a BamHI site at the 5' end of the cDNAs. After hybridisation of the vector, the cDNA and the adapter, the recombinant molecules are circularised by the action of phage T4 ligase. The single-stranded regions are then repaired by means of phage T4 DNA polymerase. The pool of plasmids thereby obtained is used to transform *E. coli* strain MC 1061 (Casabadan and S. Cohen, J. Bact. (1980), 143, 971–980) by electroporation.

Protocol for preparation of the complementary DNA library
a) Preparation of the complementary DNA From 5 µg of the RNA-poly(A)$^+$ samples of peripheral blood mononuclear cells obtained at the end of section 1, of the following composition: RNA-poly(A)$^+$-A: 0.5 µg, RNA-poly(A)$^+$-NA: 2 µg, RNA-poly(A)$^+$-T(5 h): 2 µg and RNA-poly(A)$^+$-T(24 h): 0.5 µg, the single-stranded complementary DNA labelled with [$^{32}$P]-dCTP (the complementary DNA obtained possessing a specific activity of 3000 dpm/ng) is prepared with the synthetic primer of the following sequence (SEQ ID NO:18) (comprising a BamHI site):

5'<GATCCGGGCC CTTTTTTTTT TTT<3' in the volume of 100 µl of buffer of composition: 50 mM Tris-HCl, pH 8.3, 5 mM MgCl$_2$, 10 mM DTT, containing 0.5 mM of each of the deoxynucleotide triphosphates, 100 µCi of [α-$^{32}$P]-dCTP and 100 U of RNasin (Promega). After 30 min of incubation at 46° C. with 100 units of the enzyme reverse transcriptase (Genofit-E1 022), 4 ml of 0.5M EDTA are added. The mixture is extracted a first time with phenol (saturated with TE buffer) and then a second time with chloroform. 10 µg of calf liver transfer RNA, ¹⁄₁₀ volume of 10M ammonium acetate solution and 2.5 volumes of ethanol are added to precipitate the complementary DNA. The suspension is centrifuged, the pellet is dissolved in 30 µl of TE buffer and the small molecules such as salts, phenol and chloroform are then removed by exclusion chromatography on a P10 polyacrylamide (Biogel P10—200–400 mesh, ref. 1501050—Biorad) column.

b) Alkaline hydrolysis of the RNA template 4.6 µl of 2N NaOH solution are added, the mixture is incubated for 30 min at 68° C., 4.6 µl of 2N acetic acid are then added and the solution obtained is passed through a P10 polyacrylamide column.

c) Homopolymeric addition of dG

The complementary DNA is elongated at the 3' end with a dG "tail" with 66 units of the enzyme terminal transferase (Pharmacia 27073001). Incubation is performed in 60 µl of buffer of composition: 30 mM Tris-HCl, pH 7.6, 1 mM cobalt chloride, 140 mM cacodylic acid, 0.1 mM DTT, 1 mM dGTP, for 30 min at 37° C., and 4 µl of 0.5M EDTA are then added.

d) Purification on a Sepharose CL-4B column

In order to remove the synthetic primer, the complementary DNA is purified on two successive columns of 1 ml of Sepharose CL-4B (Pharmacia), equilibrated with a 30 mM NaOH/2 mM EDTA solution.

The first three radioactive fractions (of approximately 80 µl each) are pooled and precipitated with ¹⁄₁₀ volume of 10M ammonium acetate solution and 2.5 volumes of ethanol. The amount of complementary DNA is 1 µg.

e) Hybridisation

The pellet of complementary DNA is suspended in 25 µl of TE buffer, 15 µg of RNA-poly(A)$^+$ extracted from COS line cells, then ¹⁄₁₀ volume of 3M NaCl solution and 2.5 volumes of ethanol are added and precipitation is allowed to take place at −20° C.

The suspension is centrifuged, the pellet is washed with 70% ethanol, dried and dissolved in 5 µl of buffer of the following Composition: 0.1M Tris-HCl, pH 7.5, 0.3M NaCl, 1 mM EDTA, the solution obtained is placed in a capillary tube which is sealed and the mixture is then incubated at 65° C. for 40 h.

The contents of the capillary are diluted in 100 µl of TE buffer to which 300 µl of 50 mM sodium phosphate buffer, pH 6.8, are added. The solution obtained is passed through a hydroxyapatite (Biorad ref. 130.0520) column at 60° C., equilibrated with this phosphate buffer. The single strand (unhybridised complementary DNA) and the double strand (COS messenger RNA hybridised with the complementary DNA) are separated with a phosphate buffer gradient from 0.1M to 0.2M through the hydroxyapatite column. The fractions corresponding to the single-stranded complementary DNA (25% by weight of the cDNA eluted, corresponding to an approximately 4-fold enrichment in sequences specific to peripheral blood mononuclear cells) are pooled, 20 µg of transfer RNA are added and the total volume is precipitated with ¹⁄₁₀ volume of 10M ammonium acetate solution and 2.5 volumes of ethanol. The suspension is centrifuged, the pellet is dissolved in 200 µl of TE, the residual phosphate is removed on P10 polyacrylamide and precipitation is induced again with ¹⁄₁₀ volume of 10M ammonium acetate solution and 2.5 volumes of ethanol.

The pellet is dissolved in 30 µl of a 30 mM NaOH, 2 mM EDTA solution. The complementary DNA is loaded onto a 1-ml Sepharose CL-4B (Pharmacia) column equilibrated with a 30 mM NaOH, 2 mM EDTA solution, in order to remove the remaining synthetic primer. The first 3 radioactive fractions of approximately 80 µl each are pooled. The cDNA contained in these fractions is precipitated with ¹⁄₁₀ volume of 10M ammonium acetate solution and 2.5 volumes of ethanol. The amount of complementary DNA thereby recovered is 20 ng.

f) Pairing of the cloning vector PSE1 and the complementary DNA in the presence of the adapter After centrifugation, the pellet is dissolved in 33 µl of TE buffer, 5 µl (125 ng) of cloning vector pSE1, 1 µl (120 ng) of the adapter of the following sequence (SEQ ID NO:19) (comprising an ApaI site)

5'AAAAAAAAAA AAAGGGCCCG 3' and 10 µl of 200 mM NaCl solution are added, and the reaction mixture is incubated for 5 min at 65° C. and then allow to cool to room temperature.

g) Ligation

The cloning vector and the single-stranded cDNA are ligated in a volume of 100 µl with 32.5 units of the enzyme phage T4 DNA ligase (Pharmacia ref. 270 87002) overnight at 15° C. in a buffer of composition: 50 mM Tris-HCl, pH 7.5, 10 mM $MgCl_2$, 1 mM ATP.

h) Synthesis of the second strand of the cDNA

The proteins are removed by phenol extraction followed by chloroform extraction, and 1/10 volume of 10 mM ammonium acetate solution are then added, followed by 2.5 volumes of ethanol. The mixture is centrifuged, the pellet is dissolved in the buffer of composition 33 mM Tris-acetate, pH 7.9, 62.5 mM potassium acetate, 1 mM magnesium acetate and 1 mM dithiothreitol (DTT), and the second strand of complementary DNA is synthesised in a volume of 30 µl with 30 units of the enzyme phage T4 DNA polymerase (Pharmacia, ref. 27-0718) and a mixture of 1 mM of the four deoxynucleotide triphosphates dATP, dCTP, dGTP and dTTP, as well as two units of the phage T4 gene 32 protein (Pharmacia—ref. 27-0213), for 1 h at 37° C. Phenol extraction is performed, and the traces of phenol are removed with a P10 polyacrylamide (Biogel P10—200–400 mesh—Ref 15011050—Biorad) column.

(i) Transformation by electroporation

E. coli MC1061 cells (Clontech) are transformed with the recombinant DNA obtained above by electroporation using the Biorad Gene Pulser apparatus (Biorad) employed at 2.5 kV under the conditions specified by the manufacturer, and the bacteria are then grown for 1 hour in so-called LB medium (Sambrook, op. cit.) of composition: bacto-tryptone 10 g/l, yeast extract 5 g/l, NaCl 10 g/l, and then for 6 h 30 min in LB medium with the addition of 100 µg/ml of ampicillin.

The number of independent clones is determined by plating out a 1/1000 dilution of the transformation after the 1st hour of incubation on a dish of LB medium with the addition of 1.5% of agar (w/v) and 100 µg/ml of ampicillin, referred to hereinafter as LB agar medium. The number of independent clones is 500,000.

SECTION 3

Screening of the subtracted complementary DNA library and selection of the clone NC30

1) Production of replicas of the bacterial colonies of the cDNA library on nylon filters:

Approximately 40,000 recombinant bacteria of the cDNA library are distributed on Petri dishes (245×245 mm) containing LB agar medium (approximately 2000 colonies/dish).

From each of these dishes, a transfer of the colonies onto a nylon membrane (Hybond N-Amersham) is carried out by applying the membrane to the surface of the dish and making identification marks by piercing the membrane using a needle. The membrane is then removed and applied to the surface of a fresh Petri dish containing LB agar medium. The membrane is left in place for a few hours at 37° C. to obtain regeneration of the colonies. From this first membrane, four replicas are produced on fresh membranes (applied beforehand to LB agar medium to moisten them) by successive contacts with the first membrane. The replica membranes obtained are finally applied to dishes of LB agar medium and incubated overnight at 30° C.

The replica membranes are applied, colony-side upwards, to a sheet of Whatman 3 MM saturated with a solution of composition: 0.5M NaOH, 1.5M NaCl for 5 min, which enables the bacteria to be lysed and the DNA to be bound. The replica membranes are then placed on a second sheet of Whatman 3 MM, this time saturated with a neutralising solution of composition: 1.5M NaCl, 5M Tris-HCl, pH 8.0, for 5 min. The replica membranes are then immersed in a 2× SSC solution (composition of the SSC solution: 0.15M NaCl, 0.015M sodium citrate), and the bacterial debris are partially removed by rubbing gently using cleansing wadding.

The replica membranes are then treated with proteinase K (Boehringer Mannheim GmbH) at a concentration of 100 µg/ml in a solution of composition: 10 mM Tris-HCl, pH 8, 10 mM EDTA, 50 mM NaCl, 0.1% SDS in the proportion of 20 ml per membrane. The membranes are incubated for 30 min at 37° C. with agitation. The replica membranes are immersed again in a 2× SSC solution to remove finally all trace of bacterial debris. They are lastly placed to dry on filter paper for a few minutes and then for 30 min under vacuum at +80° C. For each dish, four replica membranes, hereinafter referred to as replica 1, replica 2, replica 3 and replica 4, are thereby obtained.

2) Preparation of the RNA used for manufacture of the cDNA probes:

a) Culture and stimulation of peripheral blood mononuclear cells using PMA, (PMA and anti-CD28), (PMA, PHA-P and cyclosporin A) or (PMA and PHA-P):

Non-adherent cells are prepared as described above (section 1.1). They are cultured for 5 h in Falcon type flasks of surface area 175 $cm^2$ in the presence of RPMI medium supplemented with 10% of fetal calf serum (Gibco BRL-Ref. 013-06290H) and with the addition of 10 units of penicillin and 10 µg of streptomycin (Gibco-Ref. 043-05140D penicillin/streptomycin solution) per ml of medium, as well as L-glutamine (Gibco BRL-Ref. 043-05030D) to 2 mM final. The cells are stimulated for 5 h under one of the following stimulation conditions 1), 2), 3) and 4):

1) in the presence of 10 ng/ml of phorbol 2-myristate 3-acetate (PMA) (Sigma, ref. P8139)

2) in the presence of 10 ng/ml of PMA and 1 µg/ml of anti-CD28 monoclonal antibody (Réactifs et Systèmes S.A. ref. ACM0280NC050)

3) in the presence of 10 ng/ml of PMA, 5 µg/ml of phytohaemagglutinin (PHA-P) (Sigma, ref. L8754) and 1 µg/ml of cyclosporin A (Sandoz)

4) in the presence of 10 ng/ml of PMA and 5 µg/ml of PHA-P

It is, in effect, known that the addition of anti-CD28 antibody increases the amount of messenger RNAs of several cytokines, in particular IL-2, IFNγ, TNFα and GMCSF, by increasing the stability of their messenger RNAs (Lindsten T. et al, (1989), Science, 244, 339) in T lymphocytes, and that the immunosuppressant cyclosporin A inhibits the increase in messenger RNAs of the cytokines induced by activation with PMA and PHA-P in T lymphocytes (Thompson C. B. et al, 1989, Proc. Natl. Acad. Sci. USA, 86, 1333–1337).

The cells are collected under the above conditions of stimulation, and the cell pellets, referred to as cell pellet 1, cell pellet 2, cell pellet 3 and cell pellet 4, respectively, are retained.

b) Preparation of the poly(A)$^+$ RNA

From the above cell pellets, the RNA is extracted and the poly(A)$^+$ fraction is purified as described in section 1-2)a) and b). Four RNA-poly(A)$^+$ fractions are thereby obtained, referred to as fraction poly(A)⁺1, fraction poly(A)⁺2, fraction poly(A)⁺3 and fraction poly(A)⁺4, respectively.

3) Preparation of the radiolabelled cDNA probes:

The radiolabelled cDNA probes, referred to as probe 1, probe 2, probe 3 and probe 4, respectively, are synthesised from the four RNA-poly(A)⁺ fractions above, prepared as described below.

1 µg of poly(A)⁺ RNA is hybridised with 200 ng of oligo(dT)12–18 (pharmacia) in 2 to 3 µl of buffer of composition 50 mM Tris-HCl, pH 7.5, and 1 mM EDTA, by incubation for 2 min at 65° C. and cooling to room temperature. Synthesis of the radiolabelled cDNA is carried out in a reaction volume of 10 µl in buffer of composition: 50 mM Tris-HCl, pH 8.3, 5 mM $MgCl_2$, 10 mM dithiothreitol, containing 500 µM of each of the 3 deoxynucleotide triphosphates dATP, dGTP and dTTP (Pharmacia), 10 µM dCTP and 150 µCi of [$\alpha$-$^{32}$P]-dCTP (3000 Ci/mmol-Amersham), and 40 units of RNasin (RNAse inhibitor—Genofit). The reaction is performed at 46° C. for 30 min in the presence of 10 to 20 units of reverse transcriptase (Genofit). This synthesis is followed by the alkaline hydrolysis of the RNA with 0.3M NaOH solution in a final volume of 20 µl for 30 min at 65° C. The mixture is neutralised by adding 3M acetic acid. The volume is adjusted to 50 µl with TE medium. An extraction is performed with an equal volume of phenol, followed by a second extraction with the same volume of a chloroform/isoamyl alcohol mixture (in the respective proportions 24:1). The [$\alpha$-$^{32}$P]-dCTP not incorporated during the synthesis of the cDNA strand is removed by exclusion chromatography on a P10 polyacrylamide (Biogel— 200–400 mesh—Biorad) column.

The amount of cDNA is from 60 to 100 ng, possessing a specific activity of $1\times10^9$ dpm/µg.

4) Hybridisation of the replicas of the bacterial colonies with the cDNA probes:

The replica membranes are prehybridised for 2 h at 42° C. in a buffer of composition: 50% formamide, 6× SSC, 5× Denhardt's solution, 0.1% SDS and 100 µg/ml of sonicated salmon sperm DNA, added after denaturation for 10 min at 100° C. The replica membranes are hybridised for 2 days: replica 1 with probe 1, replica 2 with probe 2, replica 3 with probe 3 and replica 4 with probe 4, these probes being used at a concentration of 4 ng/ml in the above buffer. The 5× Denhardt's solution (see Sambrook, op. cit.) has the composition: Ficoll (type 400—Pharmacia) 1 g/l, polyvinylpyrrolidone 1 g/l and bovine serum albumin (BSA) 1 g/l.

The prehybridisation and hybridisation are performed in tubes in a hybridisation oven (Hybaid), with 25 ml and 10 ml of buffer per membrane, respectively.

The replica membranes are then washed successively several times for 15 min at 20° C. in the buffer of composition 2× SSC, 0.1% SDS and then twice for 15 min in a 0.1× SSC, 0.1% SDS solution at 55° C., dried on Whatman 3 MM paper and autoradiographed on Kodak XAR5 films.

5) Hybridisation with a mixture of oligonucleotides corresponding to most of the known cytokines:

To identify the clones which contain the DNAs complementary to the messenger RNAs of known cytokines, another series of replica membranes, prepared as described above, is hybridised with a mixture—referred to as mixture C—of 28 oligonucleotides each containing 20 nucleotides, corresponding to the complementary DNAs of the following cytokines:

Interleukin-1 α(Furutani Y. et al, 1985, Nucl. Ac. Res., 13, 5869–5882), Interleukin-1 β(Auron P. et al, 1984, Proc. Natl. Acad. Sci. USA, 81, 7907–7911), Interleukin-2 (Degrave W. et al, 1983, EMBO J., 2, 3249–3253), Interleukin-3 (Yang Y. C. et al, Cell, 1986, 47, 3–10), Interleukin-4 (Yokoto T. et al, 1986, Proc. Ntl. Acad. Sci., 83, 5894–5898), Interleukin-5 (Hirano T. et al, 1986, Nature, 324, 73–75), Interleukin-6 (May L. et al, 1986, Proc. Natl. Acad. Sci. USA, 83, 8957–8961), Interleukin-7 (Namen A. et al, 1988, Nature, 333, 571–573), Interleukin-8 (Matsushima K. et al, 1988, J. Exp. Med., 167, 1883–1893), Interleukin-9 (Yang Y. C. et al, 1989, Blood, 74, 1880–1884), TNFα (Pennica D. et al, 1984, Nature, 312, 724–729), TNFβ (Gray P. et al, 1984, Nature, 312, 721–724), GCSF (Nagata S. et al, Nature, 1986, 319, 415–418), MCSF (Kawasaki E. et al, 1985, Science, 230, 291–296), GMCSF (Wong G. et al, 1985, Science, 228, 810–815), LIF (Grough N. et al, 1988, Proc. Natl. Acad. Sci. USA, 85, 2623–2627), Interferon-α (Goeddel D. et al, 1981, Nature, 290, 20–26), Interferon-β1 (Taniguchi T. et al, 1980, Gene, 10, 11–15), Interferon-γ (Gray P. et al, 1982, Nature, 295, 503–508), TGFα (Derynck R. et al, 1984, Cell, 38, 287–297), TGFβ1 (Derynck R. et al, 1985, Nature, 316, 701–705), bFGF (Prats H. et al, 1989, Proc. Natl. Acad. Sci. USA, 86, 1836–1840), Erythropoietin (Jacobs K. et al, 1985, Nature, 313, 806–810), BCGF (Sharma S. et al, 1987, Science, 235, 1489–1492), MIF (Weiser W. et al, 1989, Proc. Natl. Acad. Sci USA, 86, 7522–7526), MCP-1 (Yoshimura T. et al, FEBS Lett., 244, 487–493), Oncostatin M (Malik N. et al, 1989, Mol. Cell. Biol., 9, 2847–2853) and EDF (Murata M. et al, 1988, Proc. Natl. Acad. Sci. USA, 85, 2434–2438).

These oligonucleotides, manufactured using the Biosearch 8700 DNA synthesiser, are coupled with horses radish peroxidase EC 1.11.17 (Boehringer Mannheim—Ref. 814–407) according to the following protocol:

- the oligonucleotides are reacted on the synthesis column with carbonyldiimidazole (Aldrich— 11, 553-3) and 1,6-diaminohexane (Aldrich—H1.169-6) according to the method of Wachter et al, 1986, Nucl. Ac. Res., 14, 7985–7994.
- after deprotection of the bases and cleavage from the support by ammoniacal treatment, the oligonucleotides are purified on an ion exchange resin (Quiagen—Diagen-500051) with the ammonium counter-ion changed to a lithium ion.
- the 5'-aminooligonucleotides are coupled to horseradish peroxidase (Boehringer Mannhelm-814407) according to the method of M. Urdea et al, Nucl. Ac. Res., 1988, 16, 4937–4956.

The mixture of oligonucleotides hybridises with approximately 10% of the clones of the library.

The clones giving a stronger autoradiographic signal with probe 2 than with probe 1, stronger with probe 4 than with probe 1 and stronger with probe 4 than with probe 3, and which do not hybridise with the mixture C, were partially sequenced as described in section 4 below. Two of these clones, hereinafter referred to as clones NC30 and NC30bis, were selected. These clones contain respectively a plasmid referred to as pSE1-NC30 and a plasmid referred to as pSE1-NC30bis.

SECTION 4

Expression of the messenger RNA of the clone NC-30 in peripheral blood mononuclear cells Non-adherent cells (consisting mainly of lymphocytes) are prepared as described in section 1-1) and stimulated as described in section 3-2)-a) with, in addition, unstimulated control cells (stimulation conditions 0)). The messenger RNAs of these cells under 5 stimulation conditions are prepared as described in Example 1-2)-a) and analysed by electrophoresis on 1% agarose gel in the presence of formaldehyde (Sambrook, op. cit.), followed by a transfer onto nylon membranes (Hybond N+—Amersham) and hybridisation according to the protocol described below.

This membrane is hybridised with a probe radiolabelled with [α-$^{32}$P]-dCTP manufactured from NC30 cDNA (Amersham) by partial cutting of the latter using DNAse I, followed by a polymerisation using the enzyme DNA polymerase I (so-called "nick-translation" technique), as described by Sambrook et al, op. cit. The hybridisation takes place at 42° C. for 16 h in an aqueous medium containing 50% of formamide, 1M NaCl, a 5× Denhardt's solution and 0.1% of SDS. The membranes are washed several times at room temperature with a 2× SSC solution containing 0.1% of SDS and then washed twice at 50° C. for 15 min with a 0.1× SSC solution containing 0.1% of SDS. The 5× Denhardt's solution has the following composition: Ficoll (type 400—Pharmacia) 1 g/l, polyvinylpyrrolidone 1 g/l and BSA 1 g/l. The 1× SSC solution contains 0.15M NaCl and 0.015M sodium citrate.

For the unstimulated cells and for the cells stimulated under the conditions 1), 2), 3) and 4), an autoradiographic band corresponding to an RNA of approximately 1.4 kb is observed. The expression of this RNA is increased in the presence of PMA (band of intensity at least 5 times as strong for the stimulation condition 1) as for the stimulation condition 0)), this increase being amplified in the additional presence of PHA-P or anti-CD28 (bands of intensity approximately 5 times as strong for the stimulation conditions 2) and 4) as for the stimulation condition 1)) and unchanged in the additional presence of PHA-P and cyclosporin (bands of similar intensity for the stimulation conditions 1) and 3)).

In another experiment performed with a purified T lymphocyte population (more than 95% pure), the expression of NC30 messenger RNA is also observed after costimulation with PMA and anti-CD28.

SECTION 5

Sequencing and analysis of the cDNA sequence of the clone NC30:

1) Sequencing of the cDNA of the clone NC30:
   a) preparation of the single-stranded DNA The clone NC30 contains the vector pSE1, which carries a cDNA between the ApaI and BamHI sites, hereinafter referred to as NC30 cDNA.

The vector pSE1, which contains the origin of replication of the phage f1, enables single-stranded DNA to be produced by culturing the clone NC30 in the presence of the bacteriophage M13K07 (Pharmacia—ref. 27-1524) in the following manner:

The clone NC30 is cultured in a 15-ml tube with agitation at 37° C. in 2 ml of 2× YT medium of composition: bacto-tryptone 16 g/l, yeast extract 10 g/l, NaCl 5 g/l (described in Sambrook et al, op. cit.), supplemented with 0.001% of thiamine and 100 µg/ml of ampicillin, to an optical density at 660 nm of approximately 0.60.

100 µl of this culture are infected with the bacteriophage M13K07 (Pharmacia—ref. 27-1524) to a multiplicity of infection of the order of 10 in a 15-ml tube. The culture is agitated at 37° C.

After 1 h, 2 ml of medium are added. The culture is then incubated for approximately 16 h at 37° C. with agitation.

1.5 ml of the culture is centrifuged in a microtube at 15,000 g for 2 min.

1 ml of supernatant is transferred to a microtube and treated with 250 µl of a 20% solution of polyethylene glycol of molecular mass 6000 containing 2.5M NaCl. The mixture is incubated for 5 min at 4° C. to facilitate precipitation of the phage, and then centrifuged for 5 min at 15,000 g. The supernatant is removed and the phage pellet is resuspended in 500 µl of buffer of composition 10 mM Tris-HCl, pH 8, 1 mM EDTA.

The suspension is extracted once with phenol saturated with 100 mM Tris-HCl, pH 8, and then twice with chloroform.

The preparation is then precipitated by adding 1/10 volume of 3M sodium acetate solution, pH 4.8, and 2.5 volumes of ethanol. The precipitation is carried out at −20° C. for a minimum of 20 min. The DNA is centrifuged for 10 min at 15,000 g, and the pellet is washed with 70% ethanol solution and then resuspended in 30 µl of buffer of composition: 10 mM Tris-HCl, pH 8, 1 mM EDTA.

b) sequencing

The sequencing reactions are carried out using the United States Biochemical sequencing kit (ref. 70770), which employs the method of Sanger et al, Proc. Ntl. Acad. Sci. USA, 1977, 14, 5463–5467. The primers used are oligonucleotides of 18 nucleotides, complementary either to the vector pSE1 in the region lying immediately at the 5' end of the NC30 cDNA, or to the NC30 cDNA sequence.

2) Analysis of the NC30 cDNA sequence:

A better understanding of the description below will be gained from FIGS. 2, 3 and 4.

Analysis of the NC30 cDNA sequence (1) NC30 cDNA contains 1282 nucleotides and terminates in a poly(A) sequence.

(2) This number of nucleotides is in agreement with the size of the corresponding messenger RNA (approximately 1.4 kb) (see section 4).

(3) At position 1264–1269, the sequence AATAAA, which corresponds to the consensus sequence described by M. Birnstiel et al, 1985, Cell, 41, 349, is a polyadenylation signal. At positions 855–861, 872–878, 1133–1139 and 1152–1158, sequences of 7 nucleotides are to be found: TATTTAT, TATTTAA, AATTTAT and TATTTAA, containing the sequence ATTTA corresponding to the consensus instability unit AUUUA described by G. Shaw et al, 1986, Cell, 46, 659–667. The complementary DNA of most of the known cytokines possess a sequence corresponding to this consensus instability unit.

(4) The DNA sequence contains an open reading frame for the translation of a protein from the ATG at position 15–17 to the TGA at position 453–455, which corresponds to a translation stop codon. In this reading frame, there are two ATG codons at positions 15–17 and 57–59, capable of initiating translation, corresponding to translated proteins of 146 and 132 amino acids, respectively. Among these, the nucleotide environment of the ATG at positions 57–59 is that which most closely resembles the consensus sequence described by Kozak M., 1978, Cell, 15, 1109–1123, for the initiation of translation in eukaryotic cells.

(5) A software to test for a signal peptide, hereinafter referred to as PS software, was developed by the Applicant on the basis of the method and information described by Von Heijne, 1986, Nucl. Ac. Res. 14, 483–490. This software predicts, in this reading frame, a hydrophobic region resembling a signal peptide and four probable protein cleavage sites, at positions 74–75 (between Thr and Thr), 86–87 (between Ala and Leu), 110–111 (between Ala and Ser) and 116–117 (between Pro and Gly). The predicted signal peptide is between one of the two Met residues capable of initiating translation and one of these four cleavage sites. The predicted mature protein (translated protein from which its signal peptide has been cleaved) hence comprises a sequence of 126, 122, 114 or 112 amino acids.

The same predictions are obtained using the University of Wisconsin's UWGCG software: Devereux et al., 1984, Nucl. Ac. Res., 12, 8711–8721-Option: Testing for a signal peptide according to the method of G. von Heijne (reference above).

Comparison with other known sequences

The already known peptide sequence most closely related to that of the sequence of 112 amino acids of the mature protein is that of the protein of 132 amino acids deduced from the cDNA of the mouse protein P 600 described by K. D. Brown et al, 1989, J. Imm., 142, 679–687. This protein is expressed in a subclass of mouse T lymphocytes: Th2 cells, activated using concanavalin A.

A comparison of these peptide sequences using the method of Needleman and Wunsch, 1970, J. Mol. Biol, 48, 443–453, employed in the University of Wisconsin's UWGCG software: Devereux et al, 1984, Nucl. Ac. Res. 12, 8711–8721, GAP option, shows that 63 amino acids out of 112 are identical, equivalent to an approximately 56% homology of identity. This algorithmic method considers all possible alignments and creates an alignment, shown in FIG. 3, in which the largest possible number of identical amino acids are paired and the number of holes in the aligned sequences is minimal.

A comparison of the nucleotide sequences by this method shows an approximately 70% homology of identity between the NC30 cDNA coding sequence and the cDNA of the mouse protein P600 (see FIG. 4).

3) Sequencing of the cDNA of the clone NC30bis:

The sequencing carried out as in above item 1) allows to find for the cDNA of the clone NC30bis the same protein sequence as for the clone NC30, except the 75th translated amino acid, which is Asp coded by GAC for the clone NC30 and Gly coded by GGC for the clone NC30bis.

SECTION 6

Analysis of the secretion in COS cells of the protein encoded by NC30 cDNA

COS cells are monkey kidney cells expressing the T antigen of the SV40 virus (Gluzman Y., Cell, 23, 1981, 175–182). These cells, which permit the replication of vectors containing the origin of replication of SV40 virus DNA (as is the case with the vector pSE1), constitute hosts of choice for studying the expression of genes in animal cells.

1) Transfection of COS cells and transient expression of the protein encoded by NC30 cDNA:

$5 \times 10^5$ COS cells are inoculated into a Petri dish 6 cm in diameter (Corning) in 5 ml of Dubelcco's modified Eagle medium, hereinafter referred to as DMEM (Gibco ref. 041–01965), which contains 0.6 g/l glutamine, 3.7 g/l NaHCO$_3$ and is supplemented with fetal calf serum (Gibco) in the proportion of 5%. After approximately 16 h of culture at 37° C. in an atmosphere containing 5% of carbon dioxide, the culture medium is removed by aspiration and the cells are washed with 3 ml of PBS buffer (Gibco phosphate-buffered saline). The following mixture is then added: 1000 µl of (DMEM+10% fetal calf serum (Gibco)), 110 µl of diethylaminoethyldextran of average molecular weight 500,000 (Pharmacia) at a concentration of 2 mg/ml, 1.1 µl of 100 mM chloroquine (Sigma) and 6 µg of plasmid DNA of the clone NC30, prepared according to the alkaline lysis technique followed by purification of the plasmid DNA on a caesium chloride gradient (Sambrook et al, op. cit.). After 5 h of incubation at 37° C. in an atmosphere containing 5% of carbon dioxide, the mixture is removed from the cells. 2 ml of PBS buffer containing 10% of dimethyl sulphoxide (spectroscopic grade, Merck) are then added. After 1 min of incubation at room temperature, the mixture is removed and the cells are washed twice with PBS and incubated in DMEM medium containing 2% of fetal calf serum. Incubation is continued for 40 h at 37° C. under an atmosphere containing 5% of carbon dioxide.

In addition, control COS cells were prepared by performing the operations described above with plasmid pSE1DNA.

2) Protein labelling:

All the operations described below are performed with COS cells transfected with plasmid DNA of the clone NC30 and control COS cells.

The culture medium is removed by aspiration and the cells are washed twice with 3 ml of PBS buffer. 5 ml of MEM medium (Minimal Eagle's Medium) without methionine (Gibco—ref. 041-01900H), supplemented with 3 g/ml of glucose and 4 mM glutamine, are added. The culture is incubated for 2 h at 37° C. The culture medium is removed and 2 ml of the same medium with the addition of 200 µCi of [$^{35}$S]methionine (Amersham ref. SJ1015) are added. The culture is incubated for 6 h at 37° C. The culture medium is removed and centrifuged for 5 min to remove cell debris and cells in suspension, and the supernatant is kept.

3) Analysis of the radiolabelled proteins of the transfected COS cells by polyacrylamide gel electrophoresis:

1 ml of the supernatant of the transfected COS cells and 9 ml of acetone are precipitated at −20° C. The suspension is centrifuged and the protein pellets are recovered. They are taken up in a buffer of composition: 0.125M Tris-HCl, pH 6.8, 4% SDS, 20% glycerol, and the mixture is heated to 100° C. for 10 min. An aliquot portion of the suspension obtained, corresponding to a radioactivity of 200,000 cpm, is analysed by electrophoresis on a 15% polyacrylamide gel in the presence of SDS, according to the technique described by U. K. Laemmli, Anal. Biochem., 1977, 78, 459. The gel is dried under vacuum. The radiolabelled proteins are visualised by autoradiography.

The presence of two extra bands for the cells transfected with plasmid DNA of the clone NC30, compared to the control cells, is observed on the autoradiogram: a sharp band of high intensity corresponding to an apparent molecular mass of 9.0±2 kDa, and a diffuse band of low intensity corresponding to an apparent molecular mass of 16.0±2 kDa. The clone NC30 hence codes for a secreted protein, hereinafter referred to as protein NC30. The apparent molecular mass for the form of the protein of the invention corresponding to the 9±2 kDa band is lower than the molecular mass calculated for the mature protein of 112 amino acids of 12,366 Da. This difference is probably caused by an unexpected electrophoretic mobility of this form of the protein of the invention.

The band of apparent molecular mass 16.0±2 kDa may correspond to an N-glycosylated form of the protein of the invention. The latter possesses, in effect, four possible N-glycosylation sites given broken underlining in FIG. 2 and corresponding to the consensus sequence described by Donner et al, 1987, J. Cell. Biol., 105, 2665.

4) Demonstration of the probable N-glycosylation of the protein of apparent molecular mass 16±2 kDa.

Labelling of the proteins is performed as in 2) above, but in the presence of 10 μg/ml of tunicamycin (Sigma ref. T7765), which is an inhibitor agent of the N-glycosylation of the proteins.

Analysis of the proteins on a polyacrylamide gel is carried out as described in 3).

The presence of only one extra band of molecular weight 9±2 kDa for the cells transfected with plasmid DNA of the clone NC30, compared to the control cells, is observed on the autoradiogram. These results show that the form of the recombinant protein observed in 3), which corresponds to a molecular weight of 16±2 kDa, is N-glycosylated.

SECTION 7

Production of the NC30 protein in COS cells $4.3 \times 10^7$ COS cells are inoculated into a cylindrical culture bottle, usually called a roller bottle, of surface area 850 cm², in 150 ml DMEM medium, which contains 0.6 g/l glutamine, 3.7 g/l NaHCO$_3$ and is supplemented with fetal calf serum (Gibco) in the proportion of 5% and then buffered with carbon dioxide.

After approximately 16 h of culture at 37° C. on a roller mixer (speed of rotation approximately 0.2 rpm), the culture medium is removed by aspiration and the cells are washed with PBS buffer (phosphate-buffered saline). The following mixture is then added: 35 ml of DMEM medium+10% fetal calf serum (Sigma), 4 ml of diethylaminoethyldextran (Pharmacia, average molecular weight 500,000 ) at a concentration of 2 mg/ml, 40 μl of 100 mM chloroquine (Sigma) and 128 μg of plasmid DNA of the clone NC30, prepared according to the alkaline lysis technique followed by purification of the plasmid DNA on a caesium chloride gradient (Sambrook et al, op. cit.). After 5 h of incubation at 37° C. in an atmosphere containing 5% of carbon dioxide, the mixture is removed from the cells. 35 ml of PBS buffer at 4° C. containing 7% of dimethyl sulphoxide (spectroscopic grade, Merck) are then added. After 1 min 30 s of rotation at room temperature, the mixture is removed and the cells are washed twice with PBS. 150 ml of DMEM medium (Sigma) containing 1% of fetal calf serum (FCS) are added per roller bottle, and the cells are incubated at 37° C. in the presence of 5% CO$_2$ (rotation at 0.2 rpm). One day after transfection, the medium is removed by aspiration and the cells are rinsed twice with PBS. 150 ml of DMEM medium (Sigma) without serum are added per roller bottle, and the roller bottles are replaced at 37° C. in the presence of 5% CO$_2$ (rotating at 0.2 rpm) for 5 days.

Harvesting takes place on day 6 after transfection. The culture medium is centrifuged at 7,000 rpm for 10 min; the supernatant is filtered through a 0.2 μm Nalgene filter.

SECTION 8

Purification of the NC30 protein produced in COS cells, and determination of its amino-terminal sequence
1) Purification of the NC30 protein The preponderant form of the recombinant protein of apparent molecular mass 9±2 kDa was purified from 500 ml of the supernatant obtained in section 7, using the following steps:

ion exchange chromatography on an S Fast Flow column (Pharmacia) (15×100 mm) equilibrated beforehand with 50 mM sodium acetate solution, pH 4.0, with 1M NaCl solution in 50 mM sodium acetate buffer, pH 4.0, at a flow rate of 2 ml/min as eluant.

the eluate is concentrated on a Centriprep 10 membrane (Amicon) to a volume of approximately 1 ml, and then subjected to (reversed-phase) HPLC chromatography on a C4 column (Bownlee) (100×2.1 mm) equilibrated beforehand with a solution containing 30% of acetonitrile and 0.1% of TFA, with a linear gradient from 30 to 70% of acetonitrile in a solution containing 0.1% of TFA. The fractions containing the recombinant protein (determined by electrophoretic analysis on polyacrylamide gel in the presence of SDS) are pooled.

2) Determination of the amino-terminal sequence of the NC30 protein of apparent molecular mass 9±2 kDa:

The protein obtained at the end of 1) was subjected to an electrophoretic analysis on 16% polyacrylamide gel in the presence of SDS. The proteins are transferred for 1 h with an intensity of 0.8 mA/cm² in a buffer of composition 25 mM Tris-borate, pH 9.0, 10% methanol onto an Immobilon membrane (Millipore), and then visualised with Coomassie blue.

The band of apparent molecular mass 9±2 kDa was cut out and introduced into an Applied Biosystems model 470 A sequencer coupled to an Applied Biosystems model 120 A phenylthiohydantoin derivative analyser.

The amino-terminal sequence obtained is the following sequence (tr$_o$) (amino acids 1–16 of SEQ ID NO:1):

Gly Pro Val Pro Pro Ser Thr Ala Leu Arg Glu
1                  5                      10
Leu Ile Glu Glu Leu
          15 which corresponds to the fourth cleavage site predicted by the PS software (see section 5 subsection 2).

SECTION 9

Construction of a vector for expression of NC30 cDNA in yeast, plasmid pEMR673 and transformation of a yeast strain using this plasmid:
1) Construction of plasmid pEMR673

Plasmid pEMR583 (described in Patent Application EP-435,776) was subjected to a complete digestion with the enzymes HindIII and BamHI. The large fragment (hereinafter referred to as fragment A), comprising the 2μ origin of replication and STB locus, the LEU2d gene, the gene for resistance to ampicillin, the origin of pBR322, the PGK gene terminator, the URA3 gene, the artificial promoter and the beginning of the prepro region of the alpha pheromone, was purified.

HindIII-BamHI fragment (hereinafter designated fragment B), comprising the end of the prepro region of the alpha pheromone and the cDNA coding for the mature protein, flanked by the BamHI restriction site at the 3' end, was obtained by amplification by the PCR technique from plasmid pSE1-NC30. The sequence of this fragment is specified in FIG. 5. The fragments A and B were ligated so as to obtain plasmid pEMR673.

a) Description of the polymerase chain reaction (PCR) technique

The polymerase chain reaction (PCR) technique is a method well known to a person skilled in the art, which enables both strands of a previously denatured DNA sequence to be copied simultaneously using two oligonucleotides as primers (see, in particular, the work by H. A. Erlich, "PCR Technology: Principles and Applications for DNA amplification" published in 1989 by Macmillan Publishers Ltd editions, United Kingdom, and that by M. A. Innis et al. "PCR Protocols" published in 1990 by Academic Press Inc. San Diego, Calif. 92101, USA). The principle of this technique is summarised below.

The PCR technique is based on the repetition of three steps, enabling hundreds of thousands of copies of the original template to be obtained after between 10 and 30 cycles using a Thermus aquaticus DNA polymerase usually referred to as Taq polymerase. The three steps are as follows:

Denaturation of the template

The double-stranded DNA is denatured to single-stranded DNA by incubation at high temperature (from 92° C. to 96° C.) for approximately 2 minutes.

Hybridisation of the primers

These primers are a pair of synthetic oligonucleotides which hybridise with the ends of the region to be amplified. The two primers hybridise with the opposite strands. The primers are added in excess so that formation of the primer-template complex is favoured.

Primer extension

The step during which Taq polymerase effects extension of the primer-template complex from 5' to 3' is performed at 72° C.

In the PCR technique, the product of interest appears in the third cycle, and it is then significantly amplified. As the cycles proceed, the amplification product rapidly becomes the template with which the primers hybridise.

b) Description of the primers used

Two synthetic oligonucleotides were prepared.

The first oligonucleotide, referred to primer 1, the sequence of which is as follows (SEQ ID NO:20):

CAGTGAATTC A AGC TTG GAT AAA AGA

| CAGTGAATTC | A | AGC | TTG | GAT | AAA | AGA |
|---|---|---|---|---|---|---|
|  |  | Ser | Leu | Asp | Lys | Arg |
|  |  | Region 1 |  |  |  |  |

| TCC | CCA | GGC | CCT | GTG | CCT | CC |
|---|---|---|---|---|---|---|
| Ser | Pro | Gly | Pro | Val | Pro |  |
|  |  | Region 2 |  |  |  |  | possesses two distinct regions: the region 1, which contains the end of the prepro region of the α pheromone modified relative to the natural sequence described by Kurjan et al, 1982, 30, 933–943 by a silent mutation which enables a HindIII cleavage site to be introduced immediately before the coding portion of the region 1 (eleventh nucleotide of the region 1), and the region 2, which is a region designed to hybridise with the coding region, corresponding to the beginning of the mature protein of 114 amino acids (see section 5), of the non-coding strand of NC30 cDNA.

The second oligonucleotide, referred to as primer 2, the sequence of which is as follows (SEQ ID NO:22):

| CGACGGATCC | CAAATAATGA TGCTTTCGAA G |
|---|---|
| Region 1 | Region 2 | also consists of two distinct regions: the region 1 which carries a BamHI site on the fourth nucleotide, and the region 2 which carries a nucleotide sequence corresponding to the untranslated 3' region of NC30 cDNA. This region is designed to hybridise with the coding strand of NC30 cDNA.

c) Production of the amplified HindIII-BamHI fragment representing the end of the prepro region of the α pheromone and the cDNA coding for the mature NC30 protein.

Plasmid pSE1-NC30, which carries the cDNA coding for the NC30 protein, is used as a template.

In a tube, 100 ng of plasmid pSE1-NC30, 100 ng of primer 1, 100 ng of primer 2 and 5 µl of 10-fold concentrated reaction mixture (final concentration: 67 mM Tris-HCl, pH 8.8, 16.6 mM $(NH_4)_2SO_4$, 1 mM β-mercaptoethanol, 6.7 mM EDTA, 0.15% Triton X -100, 2 mM $MgCl_2$, 0.2 mM dNTP, 200 ng of gelatin) are added and the volume of the mixture is then brought to 50 µl by adding water.

0.5 µl, equivalent to 2.5 units, of Taq polymerase (Boehringer Mannheim ref. 1146–173) is added. The mixture is then covered with paraffin in order to prevent evaporation of the aqueous solution.

Amplification takes place during 15 reaction cycles in which the steps of one cycle are as follows:

1 min at 94° C.→denaturation 1 min at 55° C.→hybridisation 1 min at 72° C.→polymerisation After the 15 cycles, the enzyme reaction is stopped by adding 20mM EDTA.

The DNA fragment thus amplified, which possesses the expected size of approximately 380 bp, is then isolated and purified on 1% agarose gel, subjected for dialysis to chromatography on a column of P10 polyacrylamide gel (Pharmacia), and then hydrolysed completely and simultaneously with the enzymes HindIII and BamHI according to the usual techniques well known to a person skilled in the art (Sambrook, 1983) in order to form HindIII and BamHI cohesive ends. After hydrolysis, the fragment is purified on a P10 column.

The sequence of the fragment B obtained is shown in FIG. 5. It comprises, in its portion coding for the NC30 protein, a silent mutation relative to NC30 cDNA, indicated by an asterisk in FIG. 5.

The fragments A and B were ligated so as to obtain plasmid pEMR673.

2) Transformation of yeast strain EMY761 with plasmid pEMR673 and expression of the NC30 protein by the transformed strain The strain EMY761 (Mat alpha, leu2, ura3, his3) described in Patent EP-0,408,461, and which may be obtained by plasmid clear-out of the strain deposited with the CNCM on 27th December 1989 under No. I-1021, contains mutations (leu 2 and ura 3) capable of being complemented by the defective selection marker LEU2d and the selection marker URA3, which are present in plasmid pEMR673. It was transformed with plasmid pEMR673 with selection for leucine prototrophy according to a variant of the transformation technique described by Beggs et al. (Beggs et al, 1978, Nature, 75, 104–109), which consists in subjecting the yeasts to a protoplast-formation treatment in the presence of an osmotic stabiliser, sorbitol at a concentration of 1M.

The exact transformation protocol is specified below:

a) 200 ml of YPG liquid medium (see Table 1 below) are inoculated with approximately $5 \times 10^6$ cells of a stationary-phase culture, and the culture thus inoculated is agitated overnight at 30° C.

b) When the culture reaches approximately $10^7$ cells per ml, the cells are centrifuged at 4000 rpm for 5 min and the pellet is washed with 1M sorbitol solution.

c) The cells are suspended in 5 ml of 1M sorbitol solution containing 25 mM EDTA and 50 mM dithiothreitol, and incubated for 10 min at 30° C.

d) The cells are washed once with 10 ml of 1M sorbitol solution and suspended in 20 ml of sorbitol solution.

Zymolase-100T (preparation marketed by Seykagaku Kogyo Co. Ltd., obtained by partial purification on an affinity column of the culture supernatant of *Arthrobacter luteus* and containing β-1,3-glucanase/laminaripentahydrolase) is added to a final concentration of 20 µg/ml, and the suspension is incubated at room temperature for approximately 15 min.

e) The cells are resuspended in 20 ml of a medium containing sorbitol, referred to as YPG sorbitol medium (see Table 1 below), and incubated for 20 min at 30° C. with gentle agitation.

f) The suspension is centrifuged for 3 min at 2500 rpm.

g) The cells are resuspended in 9 ml of transformation buffer of composition: 1M sorbitol, 10 mM Tris-HCl, pH 7.5 and 10 mM $CaCl_2$.

h) 0.1 ml of cells and 5 µl of DNA solution (approximately 5 µg) are added, and the suspension obtained is left for 10 to 15 minutes at room temperature.

i) 1 ml of the following solution is added: 20% polyethylene glycol PEG 4000, 10 mM Tris-HCl, pH 7.5 and 10 mM $CaCl_2$.

j) 0.1 ml of the suspension obtained in i) is poured into a tube containing solid regeneration medium without leucine (see Table 1 below), which has been melted beforehand and kept liquid at approximately 45° C. The suspension is poured into a Petri dish containing a solidified layer of 15 ml of solid regeneration medium without leucine.

The transformants begin to appear after three days. One transformant, referred to as strain EMY761 pEMR673, was selected in this manner.

Table 1

Composition and preparation of the main media used in the protocol for transformation of yeast strain EMY761
YPG liquid medium
10 g of yeast extract (Difco Bacto-yeast extract)
20 g of peptone (Difco Bacto-peptone)
20 g of glucose
   mix the ingredients in distilled water. Make the final volume to 1 l with distilled water—autoclave for 15 min at 120° C.
YPG sorbitol medium
   use the formula of YPG liquid medium to which, after autoclaving, sorbitol is added to a concentration of 1M.
solid regeneration medium without leucine
6.7 g of yeast nitrogen base without amino acids (Difco)
20 mg of adenine
20 mg of uracil
20 mg of L-tryptophan
20 mg of L-histidine
20 mg of L-arginine
20 mg of L-methionine
30 mg of L-tyrosine
30 mg of L-isoleucine
30 mg of L-lysine
50 mg of L-phenylalanine
100 mg of L-glutamic acid
150 mg of L-valine
20 g of glucose
30 g of agar
182 g of sorbitol
   mix all the ingredients in distilled water. Make the final volume to 1 l with distilled water. Autoclave for 15 min at 120° C. After autoclaving, add 200 mg of L-threonine and 100 mg of L-aspartic acid.

SECTION 10

Expression in Erlenmeyer flasks of the NC30 protein by the transformed yeast strain, and demonstration of the protein in the culture medium on polyacrylamide gel in the presence of SDS 1) Culture of the strain EMY761 pEMR673

A colony of the strain EMY761 pEMR673 (obtained in section 9) was cultured in 50 ml of liquid medium without uracil. This medium contains per 1 liter:

6.7 g of yeast nitrogen base without amino acids (Difco)

5.0 g of casein hydrolysate (Difco casamino acids)

10 9 of glucose

After one night at 30° C. with agitation, the culture was centrifuged for 10 min, and the pellet was taken up in 10 ml of sterile water and centrifuged again for 10 min. Expression of the NC30 protein was induced by taking up the cells in 50 ml of medium of the following composition:

6.7 g/l of Difco yeast nitrogen base without amino acids 5.0 g/l of casein hydrolysate (Difco casamino acids)

30.0 g/l of glycerol 30.0 g/l of galactose 10 ml/l of ethanol.

The culture was replaced at 30° C. with agitation for 24 h.

2) Analysis of the protein expressed a) Polyacrylamide gel in the presence of SDS Sample preparation A portion of the cells cultured overnight in a medium referred to as liquid medium without uracil with glucose, the composition of which is specified in Table 2 below, was centrifuged: uninduced sample. The cells cultured overnight in a medium referred to as liquid medium without uracil with ethanol, glycerol and galactose (Table 2 below) were centrifuged: induced sample. The supernatant was collected. 5 ml of 50% trichloroacetic acid containing 2 mg/ml of deoxycholate were added to 10 ml of supernatant.

The mixture was placed at a temperature of +4° C. for 30 min and then centrifuged for 30 min. The pellet was taken up in approximately 1 ml of cold acetone (+4° C.) and centrifuged again for 30 min. The pellet, after being dried, is taken up in approximately 20 µl of a buffer designated loading buffer, consisting of 0.125M Tris-HCl, pH 6.8, 4% SDS, 0.002% bromophenol blue, 20% glycerol, 10% β-mercaptoethanol, according to the protocol described by Laemmli in 1970 which is well known to a person skilled in the art. The pellet is solubilised by boiling for 15 min and then neutralised.

The samples are applied to a polyacrylamide gel in the presence of SDS and subjected to electrophoresis.
Results:

Analysis of the gel (visualisation with Coomassie blue) shows for the induced sample the presence of several additional bands compared to the uninduced sample, of which the two main bands correspond to an apparent molecular weight of 9±2 and 16±2 kDa. The other additional bands observed, which are quite numerous and diffuse, probably correspond to a variable degree of glycosylation.

The N-glycosylation of a protein by yeast is known to involve a simple N-glycosylation ("core glycosylation") in the endoplasmic reticulum and an N-hyperglycosylation ("outer-chain glycosylation") in the Golgi apparatus (R. A. Hitzeman et al, 1990, "Methods in Enzymology, No. 185", Academic Press, p. 421–440). In general, the simple N-glycosylation leads to a glycoprotein of homogeneous apparent molecular weight (one band), and the N-hyperglycosylation to a glycoprotein of heterogeneous apparent molecular weight (plurality of diffuse bands).

b) Immunoblot (Western Blot) with possible endoglycosidase H treatment

Sample preparation

A portion of the cells cultured overnight in liquid medium without uracil with glucose (Table 2) was centrifuged: uninduced sample. The cells cultured overnight in liquid medium without uracil with ethanol, with glycerol and galactose (Table 2) were centrifuged: induced sample. The supernatant was collected, 5 ml of 50% trichloroacetic acid containing 2 mg/ml of deoxycholate were added to 10 ml of supernatant.

The mixture was placed at a temperature of +4° C. for 30 min and then centrifuged for 30 min. The pellet was taken up in approximately 1 ml of cold acetone (+4° C.) and centrifuged again for 30 min. The pellet is taken up in 20 μl of a solubilisation buffer (of composition 10 mM Tris-HCl, pH 6.8, 2% β-mercaptoethanol, 1% SDS). The pellet is brought to 100° C. for 5 min.

The sample is then divided into two portions to the first 10 μl portion, 10 μl of a 50 mM sodium citrate buffer, pH 5.5, containing endoglycosidase H (5 mIU: Boehringer ref. 1088726) are added. The sample is placed at 37° C. for approximately 1 night. 20 μl of loading buffer are then added to the second 10 μl portion, 10 μl of loading buffer are added. The samples are brought to the boil for 10 min.

The samples are applied to polyacrylamide gel in the presence of SDS, and electrophoresis is performed according to the protocol of Laemmli (reference already cited).

The proteins contained in the gel are then transferred onto a nitrocellulose membrane (according to the technique of H. Towbin et al, 1979, Proc. Natl. Acad. Sci. USA, 76, 4350–4354). The immunodetection, carried out according to the protocol described in the Bio-Rad Immuno-Blot Assay Kit (ref. 170-6450), involves the following steps:

saturating the nitrocellulose membrane with a TBS buffer (Tris-buffered saline) containing 3 g/100 ml of gelatin for 30 min rinsing the membrane with a buffer designated T.TBS (TBS buffer containing 0.05% of Tween 20), twice for 5 min bringing the membrane into contact with the immune serum prepared in section 13, for 1 h at room temperature rinsing the membrane with T.TBS buffer, twice for 5 min bringing the membrane into contact with the conjugated antibody of the kit rinsing the membrane with T.TBS buffer, twice for 5 min, and once for 5 min with TBS buffer the antigen-antibody complex is visualised by bringing the membrane into contact with a developing buffer containing 5-bromo-4-chloro-3-inodolylphosphate (BCIP) and nitroblue tetrazolium (NBT)

rinsing the membrane with water.

Results:

Analysis of the immunoblot shows, for the induced sample not treated with endoglycosidase H, the presence of several additional bands compared to the uninduced sample, of which the two main bands correspond to an apparent molecular weight of 9±2 and 16±2 kDa. Other numerous and diffuse bands of higher molecular weight are also revealed. All these bands are recognised by the immune serum prepared in section 13.

In the induced sample, the band corresponding to an apparent molecular weight of 16±2 kDa tends to disappear after endoglycosidase H treatment, while the 9±2 kDa band increases in intensity under the same conditions. These results show that the protein of apparent molecular mass 16±2 kDa is N-glycosylated.

The diffuse bands of higher molecular weight also disappear, and the appearance of 2 bands corresponding to apparent molecular weights of approximately 18±2 and 20±2 kDa is noted. The forms of the NC30 protein resistant to endoglycosidase H treatment may correspond to the precursor which has retained the pro sequence of the pheromone, or to O-glycosylated forms of the NC30 protein.

Table 2

Composition and preparation of some media used for the sample preparation

Liquid medium without uracil with glucose:
6.7 g of yeast nitrogen base without amino acids (Difco)
5.0 g Of casein hydrolysate (Difco casamino acids)
10.0 g of glucose mix all the ingredients in distilled water and make to 1 l final with distilled water. Autoclave for 10 min at 120° C.

Liquid medium without uracil with ethanol, glycerol and galactose:
use the formula of the liquid medium without uracil described above but without glucose. After autoclaving, add 10 ml of 100% ethanol, 30 g of glycerol and 30 g of galactose.

SECTION 11

Production of the NC30 protein in a fermenter using the strain EMY761 pEMR673

Culturing of the strain EMY761 pEMR673 is carried out in a fermenter in the following manner:

a) Preculture phase in a conical flask with baffles

A 500-ml conical flask with baffles containing 90 ml of autoclavable-phase semi-synthetic growth medium (APSGM), supplemented with 1.28 g of MES—2-(N-morpholino)ethanesulphonic acid (Sigma M 8250)—buffer and 10 ml of filtered-phase semi-synthetic growth medium (FPSGM), is inoculated using 1 ml of culture suspension, containing 20% of glycerol, of the above strain with a cell count corresponding to an OD of 3 at λ=600 nm (on a Kontron spectrometer). The chemical compositions and the method of preparing the APSGM and FPSGM media are specified below. After 24 h of incubation with agitation at 30° C., the optical density (OD) of the culture at λ=600 nm is approximately 7.

b) Growth phase in the fermenter

The above culture is used to inoculate a 2.5 l fermenter prefilled with:
800 ml of APSGM medium
100 ml of FPSGM medium The pH of the culture is regulated by the fermenter to a set value of 5.5. Similarly, the oxygen pressure is maintained above 4000 Pa (30 mm Hg) by regulation of the agitation. Initially, the air flow rate is fixed at 1 l/min, equivalent to approximately 1 VVM, and is then increased stepwise according to requirements.

After 6 to 7 h of culture at 30° C., 72 ml of a glucose solution containing 500 g/l, equivalent to 36 g of glucose in all, are added in linear fashion during 9 h.

c) Expression phase in the fermenter 100 ml of autoclavable-phase semi-synthetic expression medium (APSEM) and 100 ml of filtered-phase semi-synthetic expression medium (FPSEM), the chemical compositions and method of preparation of which are specified below, are added to the mixture described above. Culturing is then continued for approximately 5 h without any addition. The concentrations of the three carbon sources (glycerol, galactose, ethanol) are monitored by HPLC and supplemented by sterile injections so as to approximate to the following values: glycerol 15 g/l, ethanol 15 g/l, galactose 7.5 g/l.

Between 23 and 24 h after and under induction, an OD at λ=600 nm in the region of 90 is achieved and culturing is stopped.

The culture suspension is then centrifuged at 11,500 g for 30 min. The yeast cell pellet is removed and the supernatant is stored frozen at −80° C.

CHEMICAL COMPOSITION OF THE GROWTH AND EXPRESSION MEDIA

Autoclavable-phase semi-synthetic growth medium "APSGM"

|  |  | For 800 ml final (with ultrapurified water) |
|---|---|---|
| NTA (nitrilotriacetic acid) |  | 1 g |
| $K_2SO_4$ |  | 1 g |
| NaCl |  | 0.5 g |
| $MgSO_4.7H_2O$ |  | 1.0 g |
| $CaCl_2.7H_2O$ |  | 700 mg |
| Glutamic acid |  | 3.7 g |
| HY-CASE SF (Sheffield Products) |  | 25 g |
| Leucine |  | 1.8 g |
| Histidine |  | 500 mg |
| Methionine |  | 1 g |
| Type I-S trace elements (see below) |  | 5 ml |

Adjust the pH to 5.5 with concentrated $H_2SO_4$ or concentrated KOH.
Autoclave for 20 min at 120° C.

List of type I-S trace elements

|  |  | For 1 liter final (with ultrapurified water) |
|---|---|---|
| Copper sulphate | $CuSO_4.5H_2O$ | 780 mg |
| Boric acid | $H_3BO_3$ | 5 g |
| Zinc sulphate | $ZnSO_4.7H_2O$ | 3 g |
| Potassium iodide | KI | 1 g |
| Manganese sulphate | $MnSO_4.2H_2O$ | 3.5 g |
| Sodium molybdate | $Na_2M_oO_4.2H_2O$ | 2 g |
| Ferric chloride | $FeCl_3.6H_2O$ | 4.8 g |

Add 100 ml of concentrated hydrochloric acid to the solution.
Make to 1000 ml.

Filtered-phase semi-synthetic growth medium "FPSGM"

|  | for 100 ml final (with ultrapurified water) |
|---|---|
| $KH_2PO_4$ | 4 g |
| Tryptophan | 350 mg |
| Type I-S vitamins (see below) | 1 ml |
| Glucose | 15 g |

Heat to dissolve, cool to luke warm, add the type I-S vitamins and sterilise by filtration through a 0.2 μm membrane.

List of type I-S vitamins

|  | for 100 ml final (with ultrapurified water) |
|---|---|
| Biotin | 5 mg |
| Folic acid | 4 mg |
| Niacin | 6 mg |
| (Nicotinic acid - pyridoxine HCl) | 250 mg |

CHEMICAL COMPOSITION OF THE GROWTH AND EXPRESSION MEDIA

| Thiamine HCl | 1 g |
|---|---|
| Ca pantothenate | 5 g |
| m-inositol | 10 g |

Make to 100 ml after dissolution.
Filter under sterile conditions in the cold state through a 0.2 μm membrane.
Store at a temperature of +4° C.

Autoclavable-phase semi-synthetic expression medium "APSEM"

|  | for 400 ml (with ultrapurified water) |
|---|---|
| NTA | 1 g |
| $K_2SO_4$ | 1.74 g |
| Glutamic acid | 5 g |
| HY-CASE SF (Sheffield Products) | 20 g |
| Leucine | 1.8 g |
| Histidine | 500 mg |
| Methionine | 1 g |
| Tryptophan | 350 mg |
| $MgSO_4.2H_2O$ | 600 mg |
| type I-S trace elements (see above) | 5 ml |

Adjust the pH to 5.5 with concentrated $H_2SO_4$ or KOH.
Autoclave for 20 min at a temperature of 120° C.

Filtered-phase semi-synthetic expression medium "FPSEM"

|  | For 100 ml final (with purified water) |
|---|---|
| $KH_2PO_4$ | 2 g |
| Tryptophan | 350 mg |
| Type I-S vitamins (see above) | 1 ml |
| Glycerol | 15 g |
| Ethanol | 15 g |
| Galactose | 7.5 g |

Heat to dissolve, cool to luke warm, add the vitamins and sterilise by filtration through a 0.2 μm membrane.

d) Analysis of the protein produced

Samples were prepared in a manner similar to that described in section 10 and subjected to polyacrylamide gel electrophoresis in the presence of SDS. A distribution of the bands is observed on the gel which is identical to that observed in section 10 for the induced sample.

SECTION 12

Purification of NC30 protein produced in yeast and determination of its amino-terminal sequence and peptide map 1) Purification of the two preponderant forms of the NC30 protein The two preponderant forms of the recombinant yeast protein, those of the bands corresponding to apparent molecular masses after polyacrylamide gel electrophoresis in the presence of SDS of 9±2 kDa and 16±2 kDa, were isolated and purified from 500 ml of the supernatant obtained in section 11, according to the following method:

Several steps were carried out successively:

ion exchange chromatography on a Q Fast Flow column (Pharmacia) (5×5 cm) equilibrated beforehand with 50 mM sodium acetate solution, pH 4.0. Flow rate: 1 ml/min. The pH of the supernatant is adjusted beforehand to 4.0. Under these working conditions, the protein does not bind to the gel.

ion exchange chromatography on an S Fast Flow column (Pharmacia) (5×4 cm) equilibrated beforehand with 50 mM sodium acetate solution, pH 4.0, with 1M NaCl solution in 50 mM sodium acetate buffer, pH 4.0, as eluent. Flow rate: 1 ml/min.

the eluate is concentrated on a YM5 membrane (Amicon) to a volume of approximately 2 ml, and then applied to an ACA 54 (IBF) gel filtration column (100×1.5 cm) equilibrated in 0.1M phosphate buffer containing 0.14M NaCl; flow rate: 0.2 ml/min. The fractions containing the recombinant protein (determined by electrophoretic analysis on polyacrylamide gel in the presence of SDS) are pooled.

The solution thereby obtained was subjected to an electrophoretic analysis on polyacrylamide gel in the presence of SDS and visualisation with silver nitrate. The two preponderant forms of the NC30 protein, corresponding to apparent molecular masses of 9±2 kDa and 16±2 kDa, with a degree of purity of greater than 70%, are observed. This solution was used in the tests of biological activity described below.

In another experiment, a step of reversed-phase HPLC on a C4 column (Brownlee), with a linear gradient from 30% to 70% of acetonitrile/0.1% TFA (trifluoroacetic acid) as eluent, was introduced into this purification protocol, enabling a product possessing a degree of purity of greater than 90% (estimation by electrophoretic analysis on polyacrylamide gel in the presence of SDS and visualisation with silver nitrate) to be obtained.

2) Determination of the amino-terminal sequence of the two preponderant forms of the NC30 protein The purified protein was subjected to electrophoresis on 16% polyacrylamide gel in the presence of SDS. The proteins in the gel are transferred onto an Immobilon membrane (Millipore) at 0.8 mA/cm$^2$ for 1 h in a buffer of composition 25 mM Tris-borate, pH 9.0, 10% methanol.

The two bands corresponding to apparent molecular masses of 9±2 kDa and 16±2 kDa were cut out and introduced into an Applied Biosystems model 470 A sequencer coupled to an Applied Biosystems model 120 A phenylthiohydantoin derivative analyser.

These two bands possess the same amino-terminal sequence (tr$_1$) (SEQ ID NO:23):

Ser Pro Gly Pro Val Pro Pro Ser Thr Ala Leu
1              5                   10 which is the expected amino-terminal sequence: that of the mature protein of 114 amino acids (see FIG. 2) described in section 5, the coding sequence of which is introduced into the vector pEMR673 described in section 9.

3) Determination of the peptide map of the form of the NC30 protein of apparent molecular mass 9±2 kDa The protein of apparent molecular mass 9±2 kDa was digested in the gel with porcine trypsin and the peptides were separated by reversed-phase HPLC under the following conditions:

The yeast supernatant obtained in section 11 was precipitated with trichloroacetic acid, and the precipitate, after solubilisation at 100° C. in a buffer containing SDS, was subjected to polyacrylamide gel electrophoresis. The proteins in the gel were visualised using Coomassie blue. The band of apparent molecular mass 9±2 kDa was cut out of the gel and digested with porcine trypsin in the gel according to the method described in the paper by J. Rosenfeld et al., in the process of publication, "In gel digestion of proteins for internal sequence analysis after one or two dimensional gel electrophoresis".

The tryptic peptides were then separated by reversed-phase HPLC chromatography on a Beckman Altex C18 column (0.21×25 cm) with a gradient from 1 to 70% of acetonitrile in 0.1% TFA solution during 60 min. The peaks are detected by measurement of the optical density at 218 nm.

Two fractions each corresponding to a peak, hereinafter referred to as first fraction and second fraction, were analysed using an Applied Biosystems model 470 A sequencer, as above.

The amino-terminal sequences obtained are as follows:

for the first fraction (amino acids 74–84 of SEQ ID NO:16):

Val Ser Ala Gly Gln Phe Ser Ser Leu His Val which corresponds to amino acids 108–118 of the translated NC30 protein (see FIG. 2)

for the second fraction (amino acids -2–9 and 104–106 of SEQ ID NO:16, respectively):

Ser Pro Gly Pro Val Pro Pro Ser Thr Ala Leu and

Lys Leu Phe which correspond to amino acids 33–43 and 138–140, respectively, of the translated NC30 protein (see FIG. 2).

SECTION 13

Cytoplasmic expression of the NC30 protein in E. coli and preparation of an immune serum 1) Cytoplasmic expression of the NC30 protein in E. coli A vector for expression of the methionylated mature NC30 protein of 112 amino acids in E. coli, designated pSE714.12, was constructed by insertion of a DNA fragment carrying a portion of NC30 cDNA into the vector pET3a opened at the NdeI and BamHI sites. This expression vector comprises, from 5' to 3':

the RNA polymerase promoter of the phage T7, contained in plasmid pET3a, described by Rosenberg et al, Gene, 56, 125–135 the portion of NC30 cDNA which codes for the mature protein of 112 amino acids (see section 5), preceded by an ATG translation initiator the terminator of the phage T7 gene 10 (Studier et al, J. Mol. Biol., 1986, 189, 113–130).

This expression cassette functions only in the presence of the RNA polymerase specific to the phage T7. It is hence appropriate to have this RNA polymerase synthesised in the host E. coli strain. A cassette for expression of this RNA polymerase was constructed by placing the coding sequence for this enzyme (cloned into phage lambda CE6 DNA by Studier et al, 1986, J. Mol. Biol, 189, 113–130) under the control of the lambda PR promoter. This expression cassette also comprises an allele of CI (CI857) coding for a temperature-sensitive form of the repressor of this PR promoter (P. Leplatois et al, 1983, Biochimie, 65, 317–324). Consequently, at low temperature, the cassette for expression of the DNA polymerase is repressed, and at high temperature the expression is derepressed. This expression cassette was cloned into an integration vector pEJL407 derived from the plasmids of N. Kleckner (1984, Gene, 32, 369–379). The vector obtained is plasmid pEMR648. This vector is maintained in the episomal state in the cell, but it causes the integration of one or more copies of the cassette for expression of the polymerase (including the CI repressor) when the transposition is induced with IPTG (isopropyl β-thiogalactoside). The transposase responsible for this integration is under the control of the lacI gene, but is not itself transposed, thereby enabling stable integrants to be obtained after plasmid clear-out. By transforming E. coli strain K12 HB101 (Gibco BRL—ref. 8260 SA) with pEMR648, and then causing the integration events on the transformants, a derivative of HB101 was obtained, referred to as VG112, which comprises 2 cassettes for expression of the phage T7 polymerase under the control of the temperature-sensitive PL-CI system, integrated in the chromosome. E. coli strain VG112 was cleared of plasmid pEMR648 and transformed at low temperature (30° C.) with plasmid pEMR714.

The transformant selected, referred to as strain VG112 pSE714.12, and deposited with the CNCM on 20th December 1991 under No. I-1162, was cultured on LB medium containing ampicillin at a concentration of 100 μg/ml at 30° C. to an OD at 600 nm of 1. Expression of the polymerase gene was then induced using IPTG at 41° C. for 2 h. Analysis of a total cell extract on denaturing polyacrylamide gel enabled a 9 kDa protein, corresponding to an extra band compared to the cleared and untransformed strain VG112 (control strain), to be demonstrated. Lysis of the cells by sonication followed by centrifugation enables the cell extract to be separated into 2 fractions: a soluble fraction (supernatant) and an insoluble fraction (pellet). NC30 protein is to be found with the proteins of the insoluble fraction, and represents approximately 50% (by mass) of the proteins of this fraction.

2) Preparation of an immune serum recognising the NC30 protein

This insoluble fraction was used to immunise a rabbit (New Zealand male weighing approximately 2 kg). Immunisations were performed every 15 days according to the protocol described by Vaitukaitis, 1981, Methods in Enzymology, 73, 46. For the first injection, one volume of antigen solution is emulsified with one volume of Freund's complete adjuvant (Sigma—ref. 4258). 6 boosters were administered in Freund's incomplete adjuvant (Sigma—ref. 5506).

The immune serum obtained is capable of recognising the NC30 protein produced by yeast and by COS cells, by immunodetection after polyacrylamide gel electrophoresis in the presence of SDS.

3) Characterisation of the NC30 protein by peptide mapping

The insoluble fraction obtained in 1) is subjected to polyacrylamide gel electrophoresis in the presence of SDS. The proteins in the gel are visualised by staining with Coomassie blue. The band corresponding to an apparent molecular mass of 9±2 kDa was cut out of the gel and digested with porcine trypsin in the gel, and the tryptic peptides were separated as described in section 12-3).

A fraction corresponding to a peak was analysed using an Applied Biosystems model 470A sequencer.

The amino-terminal sequence obtained is as follows (SEQ ID NO:27):

Val Ser Ala Gly Gln Phe Ser Ser Leu N Val Arg in which N represents an undetermined amino acid.

This sequence corresponds to amino acids 108–119 of the translated NC30 protein (see FIG. 2) and to the peptide of the first fraction analysed in section 12.

SECTION 14

Demonstration for the NC30 protein of an inhibitory activity with respect to the production of IL-1β and IL-6 messenger RNAs by LPS-stimulated peripheral blood monocytes 1)—Method used a) Cell preparation From a bag of peripheral blood (taken from a healthy volunteer in a blood transfusion centre), most of the red cells are removed by sedimentation at 37° C. for 30 min in a medium containing 0.6% dextran, 0.09% NaCl. The cells are then deposited on top of a layer of Ficoll-Paque (Pharmacia) and centrifuged at 400 g for 30 min. The peripheral blood mononuclear cells (PBMNC), which are present at the interface between the Ficoll and the supernatant, are withdrawn. The PBMNC are placed in RPMI medium (RPMI 1640 medium—Gibco BRL) containing 10% fetal calf serum (FCS) on culture dishes 15 cm in diameter on the basis of 1 to $5 \times 10^7$ cells per dish. After 30 min, the medium is aspirated and the cells adhering to the dish (mainly consisting of monocytes) are incubated as described below.

b) Incubation of the cells with LPS and the NC30 protein

The adherent PBMNC are incubated in 20 ml of RPMI/10% FCS for 4 h at 37° C. under an atmosphere containing 5% $CO_2$ in the presence of 5 μg per ml of lipopolysaccharide LPS (Sigma—ref. L4391) and increasing concentrations of the NC30 protein derived from purified yeast (0.1 to 10 ng/ml), or supernatants of COS cells either transfected with plasmid pSE1NC30 and cultured as described in section 7, or transfected with plasmid pSE1 and cultured under the same conditions (controls).

c) RNA preparation and analysis

The cells are washed with PBS and then scraped off directly in 1 ml of buffer D (of composition: 4M guanidinium thiocyanate, 25 mM sodium citrate, 0.5% sarcosyl, 0.1M β-mercaptoethanol: Chomczynski P. and Sacchi N. (1987), Anal. Biochem., 162, 156–159). The RNA is prepared by the phenol extraction method at acid pH described by these authors. Between 1 and 5 μg of RNA are applied to 1% agarose gel in the presence of formaldehyde (Sambrook et al, op. cit.). After migration, the RNAs are transferred onto a reinforced nitrocellulose membrane (Schleicher and Schuell) and hybridised with radiolabelled cDNA probes as in section 4. The intensities of hybridisation of each RNA with the different probes are quantified by phosphorescence analysis on a Phosphorimager apparatus (Molecular Dynamics, 800E. Arques Avenue, Sunnyvale, Calif., 94086—USA).

2)—Results

The means and the standard deviations of the results obtained with the purified NC30 protein in four experiments are collated in Table 3 below, in which the amounts of messenger RNAs measured by phosphorescence analysis are expressed as a percentage relative to the amount of messenger RNA measured for the sample originating from cells treated with LPS alone.

TABLE 3

Amount of IL-1β and IL-6 messenger RNAs measured for different concentrations of the NC30 protein

| Cell stimulation condition | Amount of messenger RNAs | |
|---|---|---|
| | IL-1β | IL-6 |
| LPS | 100 | 100 |
| LPS + NC30 protein at a concentration of 0.1 ng/ml | 97 ± 36 | 77 ± 18 |
| LPS + NC30 protein at a concentration of 1 ng/ml | 54 ± 39 | 24 ± 11 |
| LPS + NC30 protein at a concentration of 10 ng/ml | 30 ± 5 | 13 ± 4 |

On reading the above table, it is seen that the accumulation of IL-1β and IL-6 messenger RNAs in the LPS-treated monocytes is inhibited by the NC30 protein. The greatest inhibition is observed with a concentration of 10 ng/ml of NC30 protein, and the dose for obtaining a 50% inhibition ($IC_{50}$) is of the order of 1 ng/ml.

An inhibition of the production of IL-1β and IL-6 messenger RNAs is likewise seen in the presence of supernatants of COS cells transfected with plasmid pSE1-NC30, and no inhibition is seen in the presence of supernatants of control COS cells.

An inhibition of the production of IL-1β and IL-6 proteins in the culture media of monocytes treated with LPS in the presence of the NC30 protein was also seen in other experiments. IL-6 was assayed by its effect on the proliferation of the B9 hybridoma line according to the method described by L. A. Aarden, 1987, Eur. J. Immun., 17, 1411–1416. (The amount of NC30 protein present in the samples does not interfere with the assay by the line B9 of the IL-6 amounts produced by the monocytes). The assay of IL-1β was performed on EL4 cells according to the method described by E. W. Palaszynski, 1987, Biochem and Biophys. Res. Comm., 147, p. 204–211, which consists in measuring the competition of the binding with radiolabelled IL-1β.

SECTION 15

Demonstration for the NC30 protein of the modulation of the amount of CD23 surface antigen by tonsil B cells 1) Method used a) Cell preparation Human tonsils were removed after surgical operation on a 6-year-old girl. The tonsils were dilacerated with a scalpel in RPMI medium cooled to 4° C. The cells released into the medium after this operation are filtered through gauze so as to form a homogeneous cell suspension. After two washes, the cells are counted and taken up in fetal calf serum containing 10% of DMSO (Merck). $7.5 \times 10^6$ cells in a volume of 1 ml are distributed in each freezing tube. The cells are placed in a vacuum flask at −80° C. for 24 h and then stored in liquid nitrogen.

b) Incubation of the cells with the NC30 protein

On the day of the experiment, an aliquot portion of the cells is thawed at 37° C. and then diluted slowly in 50 ml of RPMI medium containing 10% of fetal calf serum. The cells are centrifuged to remove the DMSO. After cell counting, 100 μl of a cell suspension readjusted to $4 \times 10^6$ cells/ml are distributed in 96-well microtitration plates (NUNC).

The purified NC30 protein is added at different concentrations in RPMI medium containing 10% of fetal calf serum. 100 μl of the different concentrations are added to the cells in the microculture wells. Incubation is continued for 48 h at 37° C. in an atmosphere containing 5% of $CO_2$.

c) Cell labelling for immunofluorescence

After incubation, the cells are transferred to Micronics tubes (Labsystem). For single-immunofluorescence analysis, 10 μl of anti-CD23 antibody coupled to FITC (fluorescein isothiocyanate) (Immunotech) are added to the cell suspension. For double-immunofluorescence analysis, 10 μl of anti-CD23 antibody coupled to phycoerythrin and 10 μl of anti-CD20 antibody coupled to FITC (Becton Dickinson) are added simultaneously to the cell suspension.

Incubation is continued for 30 min at 4° C., the cells are then centrifuged and the pellet is taken up with 250 μl of cold PBS. 50 μl of a propidium iodide (Sigma) solution containing 20 μg/ml are added for the purpose of distinguishing the dead cells on analysis.

d) Flow cytometric analysis

The samples are analysed by fluorescence assay on a FacStar Plus cell sorter (Becton Dickinson) with a laser wavelength of fluorescence excitation of 488 nm. In single-immunofluorescence analysis, the FITC and propidium iodide emissions are collected using 530 nm and 630 nm interference filters, respectively. In double-immunofluorescence analysis, the additional emission due to phycoerythrin is collected through a 575 nm interference filter. For the latter analysis, an electronic compensation system is used to avoid contamination of the FITC fluorescence in the phycoerythrin channel, of the phycoerythrin fluorescence in the propidium iodide channel and of the propidium iodide fluorescence in the phycoerythrin channel. The results are collected and processed using the LysIS II software (Becton Dickinson).

2) Results a) Modulation of the amount of CD23 antigen on tonsil cells by the NC30 protein The means and standard deviations of the results obtained are collated in Table 4 below, for an incubation of the tonsil cells for 48 h and a concentration range of the NC30 protein from $10^{-3}$ to $10^2$ ng/ml

TABLE 4

Variation of the percentage of tonsil cells expressing the CD23 antigen in the presence of different concentrations of the NC30 protein

| Concentration of NC30 (ng/ml) | % of cells expressing CD23 |
|---|---|
| 0 | 4.8 ± 1.2 |
| $10^{-3}$ | 4.8 ± 0.8 |
| $10^{-2}$ | 4.9 ± 0.4 |
| $10^{-1}$ | 12.0 ± 2.4 |
| 1 | 17.0 ± 2.5 |
| 10 | 27.3 ± 1.6 |
| $10^2$ | 20.4 ± 2.5 |

It is seen that the percentage of tonsil cells expressing the CD23 antigen (low-affinity IgE receptor) is larger with a concentration of the NC30 protein above $10^{-1}$ ng/ml than the percentage obtained in the absence of the NC30 protein. The largest effect of this protein is seen at a concentration of 10 ng/ml.

b) Characterisation of the cells on which the NC30 protein modulates the expression of the CD23 antigen Characterisation of the cells which express the CD23 antigen was carried out by double-immunofluorescence using an anti-CD23 antibody coupled to phycoerythrin and an anti-CD20 antibody coupled to FITC. The latter antigen is directed towards a receptor present only on B cells. Flow cytometric analysis shows that only a fraction of the B cells expresses the CD23 antigen under the action of the NC30 protein.

SECTION 16

Demonstration of the action of the NC30 protein on the proliferation of hybridoma line B9

The activity of stimulation of the proliferation of hybridoma line B9 was demonstrated with culture supernatants of COS cells transfected with plasmid pSE1-NC30 (see section 7) and with the purified NC30 protein obtained from yeast (see section 12). This line is customarily used to perform a biological assay of IL-6 (L. A. Aarden, 1987, Eur. J. Immun., 17, 1411–1416).

1) Method used a) Principle of the assay

The principle of this assay is described by T. Mosman, 1983, J. Immun. Methods, 65, 55–63 and summarised below:

Mitochondria contain multiple dehydrogenases capable of reducing the tetrazolium ring to formazan. A salt of this type, MTT (3-(4,5-dimethylthiazolyl)-2,5-diphenyltetrazolium bromide), reduced in this manner gives a blue colouration with a strong absorption at 565 nm. The colorimetric assay described here enables the number of mitochondria, and hence the number of cells, to be measured quantitatively.

b) Cell culture

The cells used belong to line B9, a mouse/mouse hybridoma line described by L. A. Aarden, 1987, Eur. J. Immunol., 17, 1411–1416. They are non-adherent cells which proliferate in the presence of murine IL-6 or human IL-6.

Culture medium 500 ml of RPMI 1640 medium without glutamine ref. 041-01870M (Gibco)

50 ml of fetal calf serum (decomplemented, that is to say heated to 55° C. for 30 min to inactivate the serum complement fragments) (Sigma ref. F 4135)

12.5 ml of 100 mM sodium pyruvate ref. 043-01360H (Gibco)

2.5 ml of 1M HEPES pH 7.3 ref. 043-05630D (Gibco)

10 ml of 200 mM glutamine ref. 043-05030D (Gibco)

Immediately before use, the following are added:

β-mercaptoethanol (Sigma ref. M-6250), $5\times10^{-5}$M final;

IL-6 at a final concentration of 500 pg/ml.

c) Sample preparation:

Two types of samples were used, one obtained from the supernatant of COS cells, either transfected with plasmid pSE1-NC30 and cultured as described in section 7, or transfected with plasmid pSE1 and cultured under the same conditions (control), the other from the solution of NC30 protein obtained from yeast and purified in section 12, at a concentration of 50 ng/ml.

d) Assay protocol

The assay is performed in 96-flat-bottomed-well culture plates, each sample being assayed on a row of 12 wells at variable concentrations.

The line B9 cells are cultured, washed twice with culture medium without IL-6, resuspended in culture medium (without IL-6) and incubated for 2 h at 37° C. This incubation enables the IL-6, which is responsible for background in the assay, to be removed more completely. Finally, the cells are centrifuged again and resuspended in the above culture medium (without IL-6) at a concentration of $2\times10^5$ cells/ml.

The following are distributed successively in the 96-well plates:

50 μl of the culture medium (without IL-6) in each well (except in the first well of each row)

100 μl of the test sample in the first well of each row (with a fold 2 dilution factor from well to well)

50 μl of the cell suspension in each well (10,000 cells per well). The plates are then placed in an incubator at 37° C. under an atmosphere containing 5% of $CO_2$.

After 3 days of incubation, 10 μl of a solution of MTT (Sigma—ref. 2128) at a concentration of 5 mg/ml in PBS are added to each well under sterile conditions. The plate is replaced in the incubator. Under the microscope, it is possible to monitor the appearance of the formazan, which is produced in the form of bluish crystals by surviving cells. After four hours, the cells are dead, the supernatant in each well is drawn off with care and the crystals are dissolved with 100 ml of a 66% solution of n-propanol containing 10% of SDS and 0.04N HCl. The plates are placed for a few moments on a plate shaker in order to homogenise the colouration. Reading is then performed using a plate reader at a wavelength of 565 nm.

In place of the assay using MTT described above, it is also possible to perform cell counting under the microscope.

2) Results a) COS cell supernatant containing the NC30 protein 6 series of measurements were carried out: 3 with different COS cell supernatants containing the NC30 protein and 3 with different control COS cell supernatants, with various dilution factors of the COS supernatant solution for each series.

Figure 6:
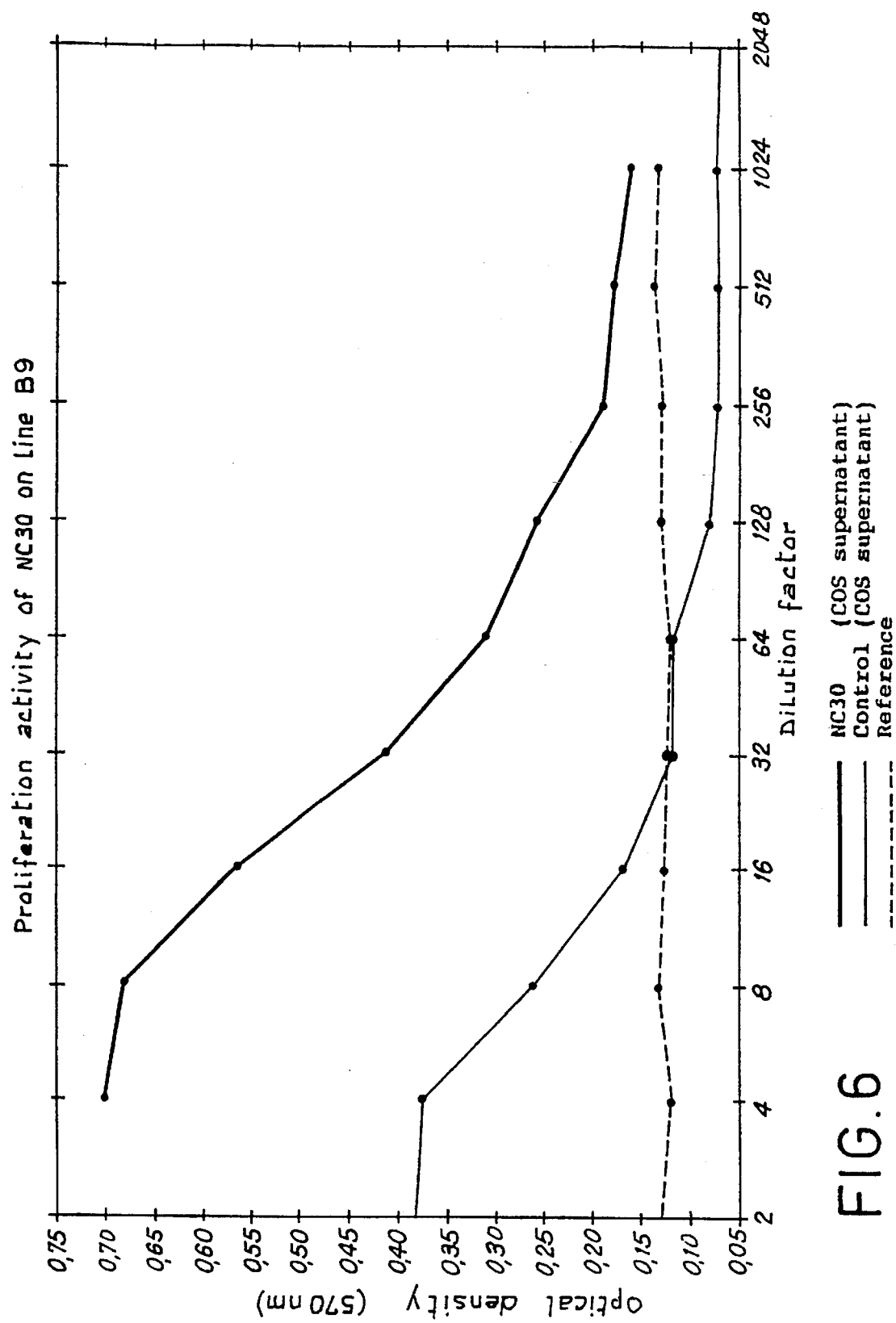
FIGS. 6 and 7 show the variation of optical density and/or cell density of the B9 line as a function of the concentration of purified protein NC30 originating from the supernatant of COS cells (FIG. 6) and from yeast (FIG. 7).

The results obtained are shown in FIG. 6, which illustrates the variation in optical density (each point is the mean of the measured optical density for the same dilution factor in the 3 series of experiments) in terms of the dilution factor of the COS supernatant solution.

It is seen on studying this figure that the COS supernatant solution containing the NC30 protein is from 4 to 6 times more active in the proliferation of line B9 than the control COS supernatant solution.

The activity of stimulation of the proliferation of line B9 seen with the control COS supernatant solution is due to the endogenous production of IL-6 by the COS cells, which may also be quantified by RIA assay (radioimmunoassay), in particular using the Amersham kit—ref: RPA 537. This RIA assay enabled it to be checked that the excess activity of stimulation of the proliferation of line B9 (by the COS supernatant containing the NC30 protein) was not linked to an overproduction of IL-6 by the COS cells.

b) Purified NC30 protein obtained from yeast:

Two series of measurements were carried out, one of the optical density after MTT staining, the other of the cell density by cell counting under the microscope, with various concentrations of the NC30 protein for each series.

Figure 7:
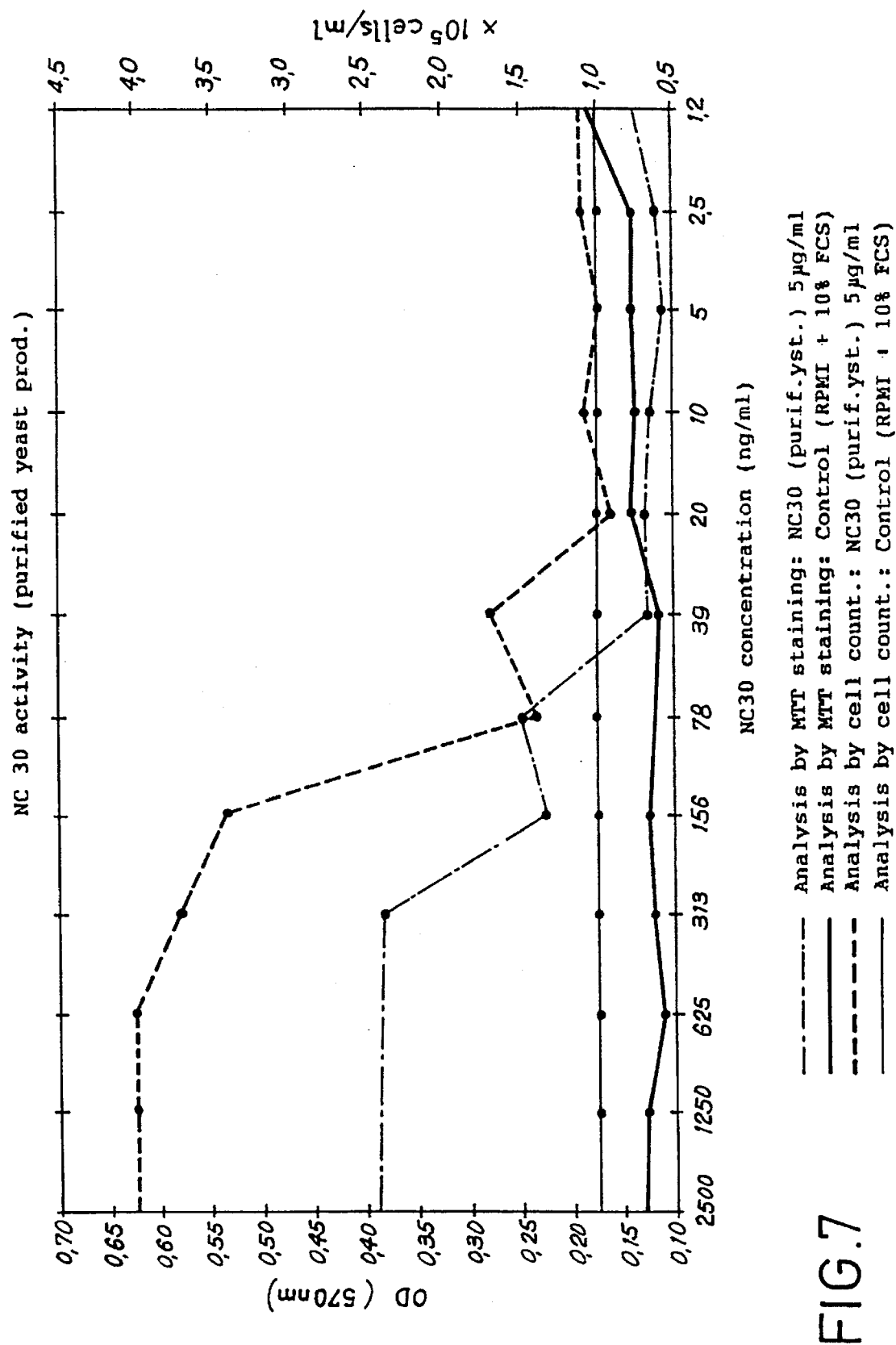

The results obtained are collated in FIG. 7, which illustrates the variation in optical density and cell density in terms of the concentration of NC30 protein expressed in ng/ml.

It is seen that the purified NC30 protein stimulates the proliferation of line B9. The $ED_{50}$ (concentration at which an activity equal to one half of the maximum activity obtained is seen) is of the order of 100 ng/ml.

It should be noted that the B9 cells are mouse cells, which may explain the need to use high concentrations of the NC30 protein compared to the concentrations used for an action on human cells (see sections 14, 15 and 17).

SECTION 17

Demonstration of the action of the NC30 protein on the proliferation of human megakaryoblastic line MO7e in the presence of GMCSF The increase in the proliferative activity of GMCSF on human megakaryoblastic line MO7e was demonstrated with the NC30 protein produced in yeast (section 12). This cell line, described by M. F. Brizzi et al., 1990, British Journal of Haematology, 76, 203–209, is strictly dependent on the cytokine IL-3 or GMCSF for its growth.

1) Method used a) Objective

The objective is to compare the proliferation of line MO7e cells cultured either in the presence of a quantity of GMCSF needed for one half of the maximal proliferation, or in the presence of the same quantity of GMCSF to which the NC30 protein is added at variable concentrations.

b) Assay principle

Cell proliferation is determined by measuring the radioactivity of the incorporation of tritiated thymidine by the cells in culture.

Proliferating cells utilise thymidine for their DNA synthesis. Tritiated thymidine introduced into the culture will compete with the "cold" thymidine in the medium and be incorporated into the cells.

After a specified time, the cells are recovered on a filter and washed to remove the excess tritiated thymidine not incorporated into the cells. Each filter is then analysed using a gamma counter. The proliferative activity is expressed as the number of dpm of tritiated thymidine incorporated.

c) Cell culture

The cells used belong to line MO7e, a human megakaryoblastic line established by M. F. Brizzi et al. (ref. cited above). They are non-adherent cells which proliferate in the presence of human IL-3 or human GMCSF. One half of the maximum activity obtained ($ED_{50}$) is:

35 pg/ml for GMCSF (Genzyme ref. RM-CSF-C) 0.7 pg/ml for IL-3 (Genzyme ref. HIL3 C)

Culture medium 500 ml of Iscove's Modified Dulbecco's Medium (IMDM medium - Gibco—ref. 04101980)

50 ml of fetal calf serum (decomplemented, that is to say heated to 55° C. for 30 min to inactivate the serum complement fragments) (Sigma ref. F4135)

10 mg/ml of gentamicin (1 ml of Gibco solution—ref. 043.05710 D)

Immediately before use, recombinant human IL-3 (Genzyme ref. HIL3.C) is added at a final concentration of 4 ng/ml.

d) Sample preparation

The test samples are prepared by dilution in the culture medium (without IL-3) of a solution of NC30 protein obtained from yeast and purified in section 12, at a concentration of 500 ng/ml.

e) Assay protocol

The assay is performed in 96-flat-bottomed-well culture plates, each sample being assayed on a row of 12 wells at variable concentrations. The line MO7e cells cultured must be in an exponential growth phase.

For the assay, the cells are washed twice with the culture medium without IL-3 and incubated for 3 h at 37° C. This incubation enables the IL-3, which is responsible for background in the assay, to be removed more fully. Finally, the cells are centrifuged again and resuspended in the above culture medium (without IL-3) at a concentration of $2\times10^5$ cells/ml The following are distributed successively in the 96-well plates:

either 50 µl of culture medium (without IL-3) in each well;

or 50 µl of culture medium (without IL-3) and 10 µl of a solution of GMCSF at a concentration of 200 pg/ml;

or 50 µl of the test sample at different concentrations and 10 µl of a solution of GMCSF at a concentration of 200 pg/ml;

and then 50 µl of cell suspension in each well (10,000 cells/well).

The plates are then placed in an incubator at 37° C. under an atmosphere containing 5% of $CO_2$.

After 3 days of incubation, 50 µl of a solution of tritiated thymidine (10 µCi/ml) (Amersham ref. TRA6=1 mCi/ml at 10 µCi/ml) in culture medium without IL-3 are added to each well under sterile conditions. The plate is replaced in the incubator. After 4 hours, the contents of each well are deposited on a filter by aspiration from the wells and washing with distilled water, and the radioactivity of the filter is measured.

2) Results

The main results obtained are collated in Table 5 below, in which the value of the radioactivity expressed in dpm for the medium without GMCSF and without NC30 protein and the value of the radioactivity for the medium containing 18 pg/ml of GMCSF appear in terms of the concentration of the NC30 protein.

The radioactivity values shown here are the means of 11 tests for the medium without GMCSF, and also the medium containing only GMCSF, and of 7 tests for the media containing GMCSF and the NC30 protein. The values of these means were compared using Student's test, with a level of significance above 99.95%.

TABLE 5

Radioactivity in terms of the concentration of NC30 protein

| Concentration of the NC30 protein (ng/ml) | 0 | 0.49 | 1.95 | 7.8 | 31.2 | 125 | 500 |
|---|---|---|---|---|---|---|---|
| Radioactivity (dpm) for medium without GMCSF | 550 | / | / | / | / | / | / |
| Radioactivity (dpm) for medium containing 18 pg/ml of GMCSF | 14462 | 16852 | 18840 | 20264 | 20549 | 20685 | 21784 |
| Significant difference with a probability >99.95% | / | no | yes | yes | yes | yes | yes |

It is seen on studying the above table that the NC30 protein significantly increases the proliferation of line MO7e in the presence of GMCSF.

SECTION 18

Demonstration of a chemotactic activity for the NC30 protein

1) Method used a) Isolation of neutrophils

Most of the red cells are removed from peripheral blood by sedimentation at 37° C. for 30 min in a solution containing 0.6% dextran T500 (Pharmacia—ref. 17-0320-01) and 0.09% NaCl. The cells are then deposited on top of a layer of Ficoll-Paque (Pharmacia) and centrifuged at 400 g for 30 min. The peripheral blood mononuclear cells (PBMNC) are present at the interface between the Ficoll and the supernatant, whereas the residual red cells and the polynuclear cells (mainly neutrophils) are in the cell pellet. This pellet is resuspended in a solution of 0.8% $NH_4Cl$, 10 mM Hepes and incubated at 37° C. for 7 min to rupture the red cells. The residual cells (mainly neutrophils) are centrifuged and washed in HBSS buffer: Hanks Balanced Saline Solution (Gibco BRL—Ref. 041-04025 H), hereinafter referred to as HBSS solution.

b) Isolation of monocytes

The principle of isolation of monocytes has been described by A. Boyum, 1983, Scan. J. Immunol., 17, 429–436. It is summarised below. The method consists in separating the monocytes from the blood using an iodinated gradient medium, Nycodenz (N,N'-bis(2,3-dihydroxypropyl)-5-[N-(2,3-dihydroxypropyl) acetamido]-2,4,6-triiodoisophthalamide). To enhance the difference in density between monocytes and lymphocytes, the osmolarity of the solution is increased so that the lymphocytes expel water and become denser. It is possible to use "NycoPrep 1.068" medium, which contains Nycodenz, sodium chloride and tricine/NaOH at optimal concentrations for the separation of monocytes (Nycomed Pharma AS, Norway—ref. 223510).

The protocol used is as follows:

Most of the red cells are removed from peripheral blood by sedimentation at 37° C. for 30 min in a solution containing 0.6% of dextran and 0.09% NaCl. The upper phase of the plasma, containing the monocytes, lymphocytes and neutrophils, is withdrawn. To separate the monocytes from the other cells, the tubes are prepared in the following manner: 6 ml of plasma are deposited on a layer of 3 ml of NycoPrep 1.068 (Nycomed Pharma AS, Norway, ref. 223510) in a tube 13–14 mm in diameter. After centrifugation at 600 g for 15 min, the clarified plasma is withdrawn up to 3–4 mm above the interphase, and the remainder of the plasma and all the NycoPrep solution are collected up to approximately 1 cm above the cell pellet, which makes it possible to avoid withdrawing the lymphocytes. The monocyte suspension collected is made up to a volume of 6–7 ml with a solution of composition 0.9% NaCl, 0.13% EDTA, 1% BSA, and then centrifuged for 7 min at 600 g.

The monocytes are contaminated with platelets. To remove the latter, the suspension is centrifuged, the supernatant is then removed and the pellet is resuspended with the same solution, repeating these operations 3 times.

The cells are resuspended in RPMI 1640 medium (Gibco) containing 0.5% bovine serum albumin (BSA).

C) Protocol for demonstrating chemotaxis

The test used is that described by W. Falk et al., 1980, J. Imm. Meth., 33, 239–247. The exact protocol used is described below:

The modified Boyden chamber marketed by Neuroprobe (ref. AP48) is used for measuring chemotaxis. The test samples, diluted in HBSS solution for the tests on neutrophils and RPMI medium containing 0.5% BSA for the tests on monocytes, are placed in the wells of the lower plate. A polycarbonate membrane (pore size: 5 mm—Nucleopore ref. 155845) is deposited on the latter with the shiny side downwards. The upper plate is deposited on the membrane. The cells (50,000 per 50 µl buffer) are placed in the wells of the upper plate. The chamber is incubated at 37° C. in a humidified incubator or in a box containing wet cotton wool for 1 h for the test on neutrophils and 3 h for the test on monocytes. The membrane is taken off and the cells which are on the dull side (cells which have not migrated) are removed by wiping the membrane and scraping it with a rubber scraper, the latter two operations being repeated once. The cells which have migrated are stained and fixed using the "Diff-quick" kit (Dade—ref. 130832). By microscopic observation, the number of cells on the shiny side of the membrane (cells which have migrated) is counted. The chemotactic index of the sample with respect to the cells in question (monocytes or neutrophils) is then calculated, this being defined as the ratio of the number of cells which have migrated towards the sample to the number of cells which have migrated in a control experiment towards the medium or dilution buffer.

3) Sample preparation a) Samples of the recombinant NC30 protein: NC30 protein obtained from yeast, purified as described in section 12, at concentrations of 0.1, 1, 10 and 100 ng/ml.

b) Control:

The peptide formyl-Met-Leu-Phe, generally referred to as fMLP (Sigma—ref. F 3506), at a concentration of 1 µM (concentration customarily employed for use as a positive control of chemotaxis).

4) Results:

The main results obtained are collated in Table 6 below, which specifies the chemotactic index with respect to monocytes and the chemotactic index with respect to neutrophils for the NC30 protein at different concentrations and the fMLP control. This index was calculated by taking the mean of four independent experiments.

TABLE 6

| NC30 protein ng/ml | Chemotactic index with respect to monocytes | Chemotactic index with respect to neutrophils |
| --- | --- | --- |
| 0.1 | 2.2 | 0.6 |
| 1 | 4.1 | 1.0 |
| 10 | 6.1 | 1.2 |
| 100 | 5.1 | 1.1 |
| fMLP 1 µM | 3.0 | 3.8 |

It is seen that, at the concentrations tested, the NC30 protein has no significant effect on neutrophils but that, at a concentration of 1, 10 and 100 ng/ml, it has a chemotactic index with respect to monocytes which is markedly higher than that of fMLP.

The NC30 protein is hence a potent and specific chemoattractant for monocytes.

SECTION 19

Immunomodulatory activity in vivo in mice

The purified NC30 protein obtained from yeast was tested for its immunomodulatory activity in two models of systemic infection in mice.

1) Materials and methods a) Animals

Female CD 1 mice supplied by C. River (France) and having an average weight of 25 g were used in this study. The groups used contain 8 or 10 mice.

b) Bacterial strains

A *Listeria monocytogenes* strain available from the Collection of the Pasteur Institute under No. CIP 5734 and an *E. coli* strain, a clinical isolate, which were stored at −70° C., were the infecting strains.

c) Samples

The NC30 protein obtained from yeast and purified as described in section 12 was used diluted in 0.15M NaCl solution containing 1% by volume of mouse plasma. This solution serves as a control.

d) Treatment of the mice

After distribution of the mice at random in several groups, the NC30 protein was administered intraperitoneally at doses of 2 and 20 µg/kg, at time intervals of 24 or 4 h before infection. The control group was treated with the diluent.

e) Models of infection

Two models of septicaemia infection employing *E. coli* and *L. monocytogenes* strains were used. These models have been described by Kong-Tek Chong, 1987, Infection and Immunity, 1987, 55, 3, p. 668–673 and M. Haakfrendscho et al., Infection and Immuunity, 1989, 57, 10, p. 3014–3021.

The E. coli and L. monocytogenes strains were cultured in a nutrient broth (Oxoid Nutrient Broth) for 18 hours at 37° C. A volume of 0.5 ml of a suitable dilution of the culture broth corresponding to $5\times10^6$ CFU (colony forming units) was administered to the mice intraperitoneally. The mortalities in different groups were recorded daily up to day ten.

f) Statistical treatment

The number of surviving mice observed in the treated groups was compared with that in the control group by the chi-squared test. The difference was considered significant when the probability was greater than 95%.

2) Results a) L. monocytogenes infection

The groups of mice treated intraperitoneally at time intervals T of 24 or 4 h before infection with 2 or 20 µg/kg of the NC30 protein behaved like the control groups. No improvement in the survival rate was seen.

b) E. coli infection

The results are collated in Table 7 below, which specifies the proportion of mice surviving in the test groups.

TABLE 7

Number of mice surviving/number of mice infected with E. coli according to the dose of NC30 protein and the time interval T separating the treatment from the infection

| T | 24 hours | 4 hours | | |
|---|---|---|---|---|
| Dose (µg/kg) | Exp. 1 | Exp. 1 | Exp. 2 | Exp. 3 |
| 0 (control) | 3/8 | 1/10 | 1/8 | 2/8 |
| 2 | 3/8 | 5/8* | 3/8 | 2/8 |
| 20 | 7/8* | not tested | 5/8* | 3/8 |

*significant difference compared to the control with a probability greater than 95%

The findings are as follows:

The mice treated intraperitoneally 24 h before infection with 20 µg/kg of the NC30 protein resisted the microbial infection significantly better than the mice in the control group.

The preventive treatment administered intraperitoneally 4 h before infection was effective in two of the three experiments carried out, and enabled a significant increase to be obtained in the survival rate of the treated animals compared to that of the control animals. In a first experiment, the only dose of 2 µg/kg tested was active. In a second experiment, only the dose of 20 µg/kg protected the mice against E. coli infection.

In another series of experiments carried out on groups of 20 mice, the following has been found: a dose of 32 µg/kg of the NC30 protein, obtained from yeast and purified as described in section 12, administered 24 hours before infection with E. Coli enabled a much higher survival rate of the (treated) mice to be obtained (11 out of 20) compared to that of the control animals (2 out of 20). The difference seen is significant with a probability greater than 99% using Student's test.

The NC30 protein hence also possesses an immunomodulatory activity in vivo.

The NC30 protein is hence a novel lymphokine possessing cytokine type immunomodulatory activity in vitro (cell proliferation, cell activation, chemotaxis and regulation of the synthesis of other cytokines) and in vivo. It acts on at least two key cells of the immune system: monocytes and B lymphocytes. It is hence a novel interkeukin. Some of its properties are held in common with interleukin-4: inhibition of the synthesis of interleukin-1β and interleukin-6 by LPS-activated human peripheral blood monocytes, and modulation of the expression of the CD23 antigen on tonsil B lymphocytes (W. Paul, 1991, Blood, 77, 1959 and Waal Malefyt et al., 1991, J. Exp. Med., 174, 1199–1220).

We claim:

1. Isolated protein comprising the amino acid sequence of SEQ ID NO:1, wherein Xaa represents Asp or Gly, and wherein said protein inhibits the production of interleukin-1β by lipopolysaccharide-stimulated peripheral blood monocytes.

2. The protein according to claim 1, further comprising a dipeptide sequence Ser Pro, wherein said dipeptide sequence is immediately upstream of said first sequence.

3. The protein according to claim 1, having an apparent molecular mass of 9.0±2 kDa, as determined by SDS-PAGE electrophoresis.

4. The protein according to claim 1, having an apparent molecular mass of 16.0±2 kDa, as determined by SDS-PAGE electrophoresis.

5. The protein according to claim 1, wherein said protein is N-glycosylated.

6. The protein according to claim 1, wherein said protein possesses a purity greater than 70%, as determined by SDS-PAGE electrophoresis and silver staining.

7. The protein according to claim 6, wherein said purity is greater than 90%.

8. The protein of claim 1, further comprising a signal sequence having the amino acid sequence of SEQ ID NO:8.

9. The protein of claim 8, wherein the C-terminus of said signal sequence immediately precedes the N-terminus of said polypeptide having the amino acid sequence of SEQ ID NO:1.

10. The protein of claim 1, further comprising a methionine residue, wherein said methionine residue immediately, precedes the N-terminus of said polypeptide having the amino acid sequence of SEQ ID NO:1.

11. Recombinant DNA comprising a coding sequence that codes for (i) a protein according to claim 1 or (ii) a precursor thereof.

12. The recombinant DNA according to claim 11, wherein said coding sequence codes for said precursor and said precursor comprises a signal sequence.

13. The recombinant DNA according to claim 12, wherein said signal sequence has an amino acid sequence selected from the group consisting of SEQ ID NO:5, SEQ ID NO:6, SEQ ID NO:7 and SEQ ID NO:8.

14. The recombinant DNA according to claim 12, wherein said signal sequence is encoded by a nucleotide sequence selected from the group consisting of SEQ ID NO:9, SEQ ID NO:10, SEQ ID NO:11 and SEQ ID NO:12.

15. The recombinant DNA according to claim 11, wherein said coding sequence comprises a polynucleotide having the nucleotide sequence of SEQ ID NO:2.

16. The recombinant DNA according to claim 11, wherein said coding sequence comprises a polynucleotide having the nucleotide sequence of SEQ ID NO:24.

17. An expression vector comprising a recombinant DNA according to claim 11.

18. A prokaryotic microorganism comprising an expression vector according to claim 17.

19. The prokaryotic microorganism of claim 18, wherein said prokaryotic microorganism belongs to the species *E. coli*.

20. Eukaryotic cells comprising the expression vector of claim 17.

21. Eukaryotic cells according to claim 20, wherein said eukaryotic cells are yeast cells.

22. Eukaryotic cells according to claim 20, wherein said eukaryotic cells are animal cells.

23. Animal cells according to claim 22, wherein said animal cells are CHO cells.

24. Animal cells according to claim 22, wherein said animal cells are COS cells.

25. A method for preparing a protein according to claim 1, comprising the steps of (i) culturing animal cells that comprise recombinant DNA encoding said protein or a precursor of said protein, said cells being capable of expressing said protein, and (ii) isolating and purifying recombinant protein expressed by said cells, wherein the culture of cells is subjected to appropriate conditions for producing said protein.

26. A method for preparing a protein according to claim 1, comprising the steps of (i) culturing yeast cells that comprise recombinant DNA encoding said protein or a precursor of said protein, said cells being capable of expressing said protein, and (ii) isolating and purifying recombinant protein expressed by said cells, wherein the culture of cells is subjected to appropriate conditions for producing said protein.

27. A composition comprising a protein according to claim 1 and a pharmaceutically acceptable carrier.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 41
        ( D ) OTHER INFORMATION: /label=Xaa
            / note= "amino acid is Asp or Gly"

( x i ) SEQUENCE DESCRIPTION: SEQ ID NO:1:

```
Gly Pro Val Pro Pro Ser Thr Ala Leu Arg Glu Leu Ile Glu Glu Leu
 1               5                  10                  15

Val Asn Ile Thr Gln Asn Gln Lys Ala Pro Leu Cys Asn Gly Ser Met
                20                  25                  30

Val Trp Ser Ile Asn Leu Thr Ala Xaa Met Tyr Cys Ala Ala Leu Glu
```

|   | 35 |   |   |   | 40 |   |   |   | 45 |   |   |   |
|---|---|---|---|---|---|---|---|---|---|---|---|---|

```
   Ser  Leu  Ile  Asn  Val  Ser  Gly  Cys  Ser  Ala  Ile  Glu  Lys  Thr  Gln  Arg
        50                  55                  60

Met  Leu  Ser  Gly  Phe  Cys  Pro  His  Lys  Val  Ser  Ala  Gly  Gln  Phe  Ser
   65                  70                  75                                  80

Ser  Leu  His  Val  Arg  Asp  Thr  Lys  Ile  Glu  Val  Ala  Gln  Phe  Val  Lys
                       85                  90                       95

Asp  Leu  Leu  Leu  His  Leu  Lys  Lys  Leu  Phe  Arg  Glu  Gly  Arg  Phe  Asn
                  100                 105                      110
```

( 2 ) INFORMATION FOR SEQ ID NO:2:

( i ) SEQUENCE CHARACTERISTICS:
        ( A ) LENGTH: 336 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GGCCCTGTGC  CTCCCTCTAC  AGCCCTCAGG  GAGCTCATTG  AGGAGCTGGT  CAACATCACC       60

CAGAACCAGA  AGGCTCCGCT  CTGCAATGGC  AGCATGGTAT  GGAGCATCAA  CCTGACAGCT      120

GACATGTACT  GTGCAGCCCT  GGAATCCCTG  ATCAACGTGT  CAGGCTGCAG  TGCCATCGAG      180

AAGACCCAGA  GGATGCTGAG  CGGATTCTGC  CCGCACAAGG  TCTCAGCTGG  GCAGTTTTCC      240

AGCTTGCATG  TCCGAGACAC  CAAAATCGAG  GTGGCCCAGT  TTGTAAAGGA  CCTGCTCTTA      300

CATTTAAAGA  AACTTTTTCG  CGAGGGACGG  TTCAAC                                  336
```

( 2 ) INFORMATION FOR SEQ ID NO:3:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
   Met  Ala  Pro  Ser  Gly  Lys  Ser  Thr  Leu  Leu  Leu  Leu  Phe  Leu  Leu  Leu
   1                   5                   10                          15

Cys  Leu  Pro  Ser  Trp  Asn  Ala  Gly  Ala
                  20                  25
```

( 2 ) INFORMATION FOR SEQ ID NO:4:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
   Met  Ser  Ser  Pro  Leu  Lys  Asn  Ala  Leu  Val  Thr  Ala  Met  Leu  Ala  Gly
   1                   5                   10                          15

Gly  Ala  Leu  Ser  Ser  Pro  Thr  Lys  Gln  His  Val  Gly  Ile  Pro  Val  Asn
                       20                  25                          30

Ala  Ser  Pro  Glu  Val  Gly  Pro  Gly  Lys  Tyr  Ser  Phe  Lys  Gln  Val  Arg
                  35                  40                       45

Asn  Pro  Asn  Tyr  Lys  Phe  Asn  Gly  Pro  Leu  Ser  Val  Lys  Lys  Thr  Tyr
             50                  55                  60
```

```
        Leu  Lys  Tyr  Gly  Val  Pro  Ile  Pro  Ala  Trp  Leu  Glu  Asp  Ala  Val  Gln
        65                  70                       75                            80

Asn  Ser  Thr  Ser  Gly  Leu  Ala  Glu  Arg
                            85
```

( 2 ) INFORMATION FOR SEQ ID NO:5:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
        Met  His  Pro  Leu  Leu  Asn  Pro  Leu  Leu  Leu  Ala  Leu  Gly  Leu  Met  Ala
        1                   5                        10                           15

Leu  Leu  Leu  Thr  Thr  Val  Ile  Ala  Leu  Thr  Cys  Leu  Gly  Gly  Phe  Ala
                       20                       25                       30
```

( 2 ) INFORMATION FOR SEQ ID NO:6:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
        Met  His  Pro  Leu  Leu  Asn  Pro  Leu  Leu  Leu  Ala  Leu  Gly  Leu  Met  Ala
        1                   5                        10                           15

Leu  Leu  Leu  Thr  Thr  Val  Ile  Ala  Leu  Thr  Cys  Leu  Gly  Gly  Phe  Ala
                       20                       25                       30

Ser  Pro
```

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
        Met  Ala  Leu  Leu  Leu  Thr  Thr  Val  Ile  Ala  Leu  Thr  Cys  Leu  Gly  Gly
        1                   5                        10                           15

Phe  Ala
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
        Met  Ala  Leu  Leu  Leu  Thr  Thr  Val  Ile  Ala  Leu  Thr  Cys  Leu  Gly  Gly
        1                   5                        10                           15

Phe  Ala  Ser  Pro
                  20
```

( 2 ) INFORMATION FOR SEQ ID NO:9:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
ATGCATCCGC  TCCTCAATCC  TCTCCTGTTG  GCACTGGGCC  TCATGGCGCT  TTTGTTGACC        60
ACGGTCATTG  CTCTCACTTG  CCTTGGCGGC  TTTGCC                                    96
```

( 2 ) INFORMATION FOR SEQ ID NO:10:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
ATGCATCCGC  TCCTCAATCC  TCTCCTGTTG  GCACTGGGCC  TCATGGCGCT  TTTGTTGACC        60
ACGGTCATTG  CTCTCACTTG  CCTTGGCGGC  TTTGCCTCCC  CA                           102
```

( 2 ) INFORMATION FOR SEQ ID NO:11:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
ATGGCGCTTT  TGTTGACCAC  GGTCATTGCT  CTCACTTGCC  TTGGCGGCTT  TGCC              54
```

( 2 ) INFORMATION FOR SEQ ID NO:12:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
ATGGCGCTTT  TGTTGACCAC  GGTCATTGCT  CTCACTTGCC  TTGGCGGCTT  TGCCTCCCCA        60
```

( 2 ) INFORMATION FOR SEQ ID NO:13:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

```
AGCTGGCTCG  CATCTCTCCT  TCACGCGCCC  GCCGCCCTAC  CTGAGGCCGC  CATCCACGCC        60
GGTGAGTCGC  GTTCTGCCGC  CTCCCGCCTG  TGGTGCCTCC  TGAACTGCGT  CCGCCGTCTA       120
```

```
GGTAGGCTCC AAGGGAGCCG GACAAAGGCC CGGTCTCGAC CTGAGCTCTA AACTTACCTA       180

GACTCAGCCG GCTCTCCACG CTTTGCCTGA CCCTGCTTGC TCAACTCTAC GTCTTTGTTT       240

CGTTTTCTGT TCTGCGCCGT TACAACTTCA AGGTATGCGC TGGGACCTGG CAGGCGGCAT       300

CTGGGACCCC TAGGAAGGGC TTGGGGGTCC TCGTGCCCAA GGCAGGGAAC ATAGTGGTCC       360

CAGGAAGGGG AGCAGAGGCA TCAGGGTGTC CACTTGTCT CCGCAGCTCC TGAGCCTGCA        420

GA                                                                     422
```

(2) INFORMATION FOR SEQ ID NO:14:

(i) SEQUENCE CHARACTERISTICS:
        (A) LENGTH: 77 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

```
AGCTTGTCGA CTAATACGAC TCACTATAGG GCGGCCGCGG GCCCCTGCAG GAATTCGGAT        60

CCCCCGGGTG ACTGACT                                                       77
```

(2) INFORMATION FOR SEQ ID NO:15:

(i) SEQUENCE CHARACTERISTICS:
        (A) LENGTH: 1297 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 15..452

(ix) FEATURE:
        (A) NAME/KEY: mat_peptide
        (B) LOCATION: 117..452

(xi) SEQUENCE DESCRIPTION: SEQ ID NO:15:

```
AAGCCACCCA GCCT ATG CAT CCG CTC CTC AAT CCT CTC CTG TTG GCA CTG          50
                Met His Pro Leu Leu Asn Pro Leu Leu Leu Ala Leu
                -34             -30                     -25

GGC CTC ATG GCG CTT TTG TTG ACC ACG GTC ATT GCT CTC ACT TGC CTT          98
Gly Leu Met Ala Leu Leu Leu Thr Thr Val Ile Ala Leu Thr Cys Leu
        -20                 -15                     -10

GGC GGC TTT GCC TCC CCA GGC CCT GTG CCT CCC TCT ACA GCC CTC AGG         146
Gly Gly Phe Ala Ser Pro Gly Pro Val Pro Pro Ser Thr Ala Leu Arg
    -5              1               5                       10

GAG CTC ATT GAG GAG CTG GTC AAC ATC ACC CAG AAC CAG AAG GCT CCG         194
Glu Leu Ile Glu Glu Leu Val Asn Ile Thr Gln Asn Gln Lys Ala Pro
                15                  20                  25

CTC TGC AAT GGC AGC ATG GTA TGG AGC ATC AAC CTG ACA GCT GAC ATG         242
Leu Cys Asn Gly Ser Met Val Trp Ser Ile Asn Leu Thr Ala Asp Met
            30              35                  40

TAC TGT GCA GCC CTG GAA TCC CTG ATC AAC GTG TCA GGC TGC AGT GCC         290
Tyr Cys Ala Ala Leu Glu Ser Leu Ile Asn Val Ser Gly Cys Ser Ala
        45              50              55

ATC GAG AAG ACC CAG AGG ATG CTG AGC GGA TTC TGC CCG CAC AAG GTC         338
Ile Glu Lys Thr Gln Arg Met Leu Ser Gly Phe Cys Pro His Lys Val
    60              65                  70
```

```
TCA GCT GGG CAG TTT TCC AGC TTG CAT GTC CGA GAC ACC AAA ATC GAG        386
Ser Ala Gly Gln Phe Ser Ser Leu His Val Arg Asp Thr Lys Ile Glu
75               80                  85                  90

GTG GCC CAG TTT GTA AAG GAC CTG CTC TTA CAT TTA AAG AAA CTT TTT        434
Val Ala Gln Phe Val Lys Asp Leu Leu Leu His Leu Lys Lys Leu Phe
             95                 100                 105

CGC GAG GGA CGG TTC AAC TGAAACTTCG AAAGCATCAT TATTTGCAGA               482
Arg Glu Gly Arg Phe Asn
            110

GACAGGACCT GACTATTGAA GTTGCAGATT CATTTTTCTT TCTGATGTCA AAAATGTCTT       542
GGGTAGGCGG GAAGGAGGGT TAGGGAGGGG TAAAATTCCT TAGCTTAGAC CTCAGCCTGT       602
GCTGCCCGTC TTCAGCCTAG CCGACCTCAG CCTTCCCCTT GCCCAGGGCT CAGCCTGGTG       662
GGCCTCCTCT GTCCAGGGCC CTGAGCTCGG TGGACCCAGG GATGACATGT CCCTACACCC       722
CTCCCCTGCC CTAGAGCACA CTGTAGCATT ACAGTGGGTG CCCCCCTTGC CAGACATGTG       782
GTGGGACAGG GACCCACTTC ACACACAGGC AACTGAGGCA GACAGCAGCT CAGGCACACT       842
TCTTCTTGGT CTTATTTATT ATTGTGTGTT ATTTAAATGA GTGTGTTTGT CACCGTTGGG       902
GATTGGGGAA GACTGTGGCT GCTGGCACTT GGAGCCAAGG GTTCAGAGAC TCAGGGCCCC       962
AGCACTAAAG CAGTGGACCC CAGGAGTCCC TGGTAATAAG TACTGTGTAC AGAATTCTGC      1022
TACCTCACTG GGGTCCTGGG GCCTCGGAGC CTCATCCGAG GCAGGGTCAG GAGAGGGGCA      1082
GAACAGCCGC TCCTGTCTGC CAGCCAGCAG CCAGCTCTCA GCCAACGAGT AATTTATTGT      1142
TTTTCCTCGT ATTTAAATAT TAAATATGTT AGCAAAGAGT TAATATATAG AAGGGTACCT      1202
TGAACACTGG GGGAGGGGAC ATTGAACAAG TTGTTTCATT GACTATCAAA CTGAAGCCAG      1262
AAATAAAGTT GGTGACAGAT AAAAAAAAAA AAAA                                  1297
```

( 2 ) INFORMATION FOR SEQ ID NO:16:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met His Pro Leu Leu Asn Pro Leu Leu Leu Ala Leu Gly Leu Met Ala
-34              -30                 -25                 -20

Leu Leu Leu Thr Thr Val Ile Ala Leu Thr Cys Leu Gly Gly Phe Ala
             -15                 -10                  -5

Ser Pro Gly Pro Val Pro Pro Ser Thr Ala Leu Arg Glu Leu Ile Glu
             1               5                  10

Glu Leu Val Asn Ile Thr Gln Asn Gln Lys Ala Pro Leu Cys Asn Gly
15                  20                  25                  30

Ser Met Val Trp Ser Ile Asn Leu Thr Ala Asp Met Tyr Cys Ala Ala
                35                  40                  45

Leu Glu Ser Leu Ile Asn Val Ser Gly Cys Ser Ala Ile Glu Lys Thr
             50                  55                  60

Gln Arg Met Leu Ser Gly Phe Cys Pro His Lys Val Ser Ala Gly Gln
             65                  70                  75

Phe Ser Ser Leu His Val Arg Asp Thr Lys Ile Glu Val Ala Gln Phe
    80                  85                  90

Val Lys Asp Leu Leu Leu His Leu Lys Lys Leu Phe Arg Glu Gly Arg
95                  100                 105                 110

Phe Asn
```

( 2 ) INFORMATION FOR SEQ ID NO:17:

( i ) SEQUENCE CHARACTERISTICS:
       ( A ) LENGTH: 384 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:17:

| | | | | | | |
|---|---|---|---|---|---|---|
| AGCTTGGATA | AAAGATCCCC | AGGCCCTGTG | CCTCCCTCTA | CGGCCCTCAG | GGAGCTCATT | 60 |
| GAGGAGCTGG | TCAACATCAC | CCAGAACCAG | AAGGCTCCGC | TCTGCAATGG | CAGCATGGTA | 120 |
| TGGAGCATCA | ACCTGACAGC | TGACATGTAC | TGTGCAGCCC | TGGAATCCCT | GATCAACGTG | 180 |
| TCAGGCTGCA | GTGCCATCGA | GAAGACCCAG | AGGATGCTGA | GCGGATTCTG | CCCGCACAAG | 240 |
| GTCTCAGCTG | GGCAGTTTTC | CAGCTTGCAT | GTCCGAGACA | CCAAAATCGA | GGTGGCCCAG | 300 |
| TTTGTAAAGG | ACCTGCTCTT | ACATTAAAG | AAACTTTTC | GCGAGGGACG | GTTCAACTGA | 360 |
| AACTTCGAAA | GCATCATTAT | TTGG | | | | 384 |

( 2 ) INFORMATION FOR SEQ ID NO:18:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( x i ) SEQUENCE DESCRIPTION: SEQ ID NO:18:

GATCCGGGCC CTTTTTTTTT TTT                         23

( 2 ) INFORMATION FOR SEQ ID NO:19:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:19:

AAAAAAAAAA AAAGGGCCCG                             20

( 2 ) INFORMATION FOR SEQ ID NO:20:

( i ) SEQUENCE CHARACTERISTICS:
       ( A ) LENGTH: 46 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: NO ( i x ) FEATURE:
       ( A ) NAME/KEY: CDS
       ( B ) LOCATION: 12..44

( x i ) SEQUENCE DESCRIPTION: SEQ ID NO:20:

```
CAGTGAATTC A AGC TTG GAT AAA AGA TCC CCA GGC CCT GTG CCT          44
              Ser Leu Asp Lys Arg Ser Pro Gly Pro Val Pro
                1           5                   10

CC                                                                 46
```

( 2 ) INFORMATION FOR SEQ ID NO:21:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Ser Leu Asp Lys Arg Ser Pro Gly Pro Val Pro
 1           5                   10
```

( 2 ) INFORMATION FOR SEQ ID NO:22:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:22:

```
CGACGGATCC  CAAATAATGA  TGCTTTCGAA  G                             31
```

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:23:

```
    Ser Pro Gly Pro Val Pro Pro Ser Thr Ala Leu
     1           5                   10
```

( 2 ) INFORMATION FOR SEQ ID NO:24:

( i ) SEQUENCE CHARACTERISTICS:
        ( A ) LENGTH: 336 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
GGCCCTGTGC  CTCCCTCTAC  AGCCCTCAGG  GAGCTCATTG  AGGAGCTGGT  CAACATCACC   60
CAGAACCAGA  AGGCTCCGCT  CTGCAATGGC  AGCATGGTAT  GGAGCATCAA  CCTGACAGCT  120
GGCATGTACT  GTGCAGCCCT  GGAATCCCTG  ATCAACGTGT  CAGGCTGCAG  TGCCATCGAG  180
AAGACCCAGA  GGATGCTGAG  CGGATTCTGC  CCGCACAAGG  TCTCAGCTGG  CAGTTTTCC   240
AGCTTGCATG  TCCGAGACAC  CAAAATCGAG  GTGGCCCAGT  TTGTAAAGGA  CCTGCTCTTA  300
```

CATTTAAAGA AACTTTTTCG CGAGGGACGG TTCAAC    336

( 2 ) INFORMATION FOR SEQ ID NO:25:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Ala Leu Trp Val Thr Ala Val Leu Ala Leu Ala Cys Leu Gly Gly
  1               5                  10                  15
Leu Ala Ala Pro Gly Pro Val Pro Arg Ser Val Ser Leu Pro Leu Thr
             20                  25                  30
Leu Lys Glu Leu Ile Glu Glu Leu Ser Asn Ile Thr Gln Asp Gln Thr
         35                  40                  45
Pro Leu Cys Asn Gly Ser Met Val Trp Ser Val Asp Leu Ala Ala Gly
     50                  55                  60
Gly Phe Cys Val Ala Leu Asp Ser Leu Thr Asn Ile Ser Asn Cys Asn
 65                  70                  75                  80
Ala Ile Tyr Arg Thr Gln Arg Ile Leu His Gly Leu Cys Asn Arg Lys
                 85                  90                  95
Ala Pro Thr Thr Val Ser Ser Leu Pro Asp Thr Lys Ile Glu Val Ala
                100                 105                 110
His Phe Ile Thr Lys Leu Leu Ser Tyr Thr Lys Gln Leu Phe Arg His
                115                 120                 125
Gly Pro Phe
        130
```

( 2 ) INFORMATION FOR SEQ ID NO:26:

( i ) SEQUENCE CHARACTERISTICS:
        ( A ) LENGTH: 447 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

```
AGCCCACAGT TCTACAGCTC CCTGGTTCTC TCACTGGCTC TGGGCTTCAT GGCGCTCTGG     60
GTGACTGCAG TCCTGGCTCT TGCTTGCCTT GGTGGTCTCG CCGCCCAGG  GCCGGTGCCA    120
AGATCTGTGT CTCTCCCTCT GACCCTTAAG GAGCTTATTG AGGAGCTGAG CAACATCACA    180
CAAGACCAGA CTCCCCTGTG CAACGGCAGC ATGGTATGGA GTGTGGACCT GGCCGCTGGC    240
GGGTTCTGTG TAGCCCTGGA TTCCCTGACC AACATCTCCA ATTGCAATGC CATCTACAGG    300
ACCCAGAGGA TATTGCATGG CCTCTGTAAC CGCAAGGCCC CCACTACGGT CTCCAGCCTC    360
CCCGATACCA AAATCGAAGT AGCCCACTTT ATAACAAAAC TGCTCAGCTA CACAAAGCAA    420
CTGTTTCGCC ACGGCCCCTT CTAATGA                                       447
```

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide (xi) SEQUENCE DESCRIPTION: SEQ ID NO:27:

```
Val Ser Ala Gly Gln Phe Ser Ser Leu Xaa Val Arg
1               5                   10
```